United States Patent [19]
Boyd et al.

[11] Patent Number: 5,959,221
[45] Date of Patent: Sep. 28, 1999

[54] AUTOMATIC CLOSED TUBE SAMPLER

[75] Inventors: Robert Boyd, Boulder; Brad Filkins, Lafayette; Gregory Gates, Golden; Mark Holubar, Boulder; Steven Zimmerman, Longmont; Mark Montognese, Longmont; Douglas Walter, Longmont; Lindsay Wert, Denver, all of Colo.

[73] Assignee: Bayer Corporation, Tarrytown, N.Y.

[21] Appl. No.: 09/018,369

[22] Filed: Feb. 4, 1998

Related U.S. Application Data

[62] Division of application No. 08/822,585, Mar. 20, 1997, Pat. No. 5,861,563.

[51] Int. Cl.⁶ .................................................. G01N 1/00
[52] U.S. Cl. ...................................... 73/864.24; 422/104
[58] Field of Search ............. 73/864.21, 864.23–864.25, 73/864.31; 422/63, 65, 100, 104; 366/140, 143, 220, 237; 220/507, 509

[56] References Cited

U.S. PATENT DOCUMENTS

| | | | |
|---|---|---|---|
| 3,897,216 | 7/1975 | Jones | 23/259 |
| 3,955,436 | 5/1976 | Tucker et al. | 73/421 |
| 3,977,794 | 8/1976 | Liedholz | 356/244 |
| 4,007,013 | 2/1977 | Kotacka | 23/259 |
| 4,165,484 | 8/1979 | Haynes | 324/71 CP |
| 4,276,258 | 6/1981 | Ginsberg et al. | 422/64 |
| 4,276,260 | 6/1981 | Drbal et al. | 422/100 |
| 4,311,484 | 1/1982 | Fosslien | 73/864.21 |
| 4,341,736 | 7/1982 | Drbal et al. | 422/100 |
| 4,387,076 | 6/1983 | Cabrera et al. | 422/67 |
| 4,475,411 | 10/1984 | Wellerfors | 73/864.24 |
| 4,495,149 | 1/1985 | Iwata et al. | 422/65 |
| 4,503,385 | 3/1985 | Haynes | 324/71.4 |
| 4,534,465 | 8/1985 | Rothermel et al. | 206/443 |
| 4,582,990 | 4/1986 | Stevens . | |
| 4,609,017 | 9/1986 | Coulter et al. | 73/864.21 |
| 4,729,876 | 3/1988 | Hennessy et al. | 422/103 |
| 4,752,690 | 6/1988 | James | 250/349 |
| 4,756,201 | 7/1988 | Uffenheimer | 73/864.83 |
| 4,799,393 | 1/1989 | Uffenheimer | 73/864.22 |
| 4,811,611 | 3/1989 | Uffenheimer | 73/864.22 |
| 4,861,554 | 8/1989 | Sakuma . | |
| 5,040,890 | 8/1991 | North, Jr. | 356/72 |
| 5,128,105 | 7/1992 | Berthold et al. | 422/104 |
| 5,137,693 | 8/1992 | Mawhirt | 422/104 |
| 5,167,926 | 12/1992 | Kirmura et al. | 422/67 |
| 5,201,232 | 4/1993 | Uffenheimer | 73/864.23 |
| 5,665,309 | 9/1997 | Champseix et al. | 422/104 |
| 5,670,117 | 9/1997 | Erb et al. | 422/104 |
| 5,700,429 | 12/1997 | Buhler et al. | 422/104 |

*Primary Examiner*—Robert Raevis
*Attorney, Agent, or Firm*—Orrick, Herrington & Sutcliffe LLP

[57] ABSTRACT

An apparatus for transporting racks of sealed sample tubes, mixing a sample material contained within the tubes, and aspirating samples from the tubes. The apparatus includes a car which runs along a rail. The car drives racks containing the sample tubes into a mixer channel disposed above and running parallel to the rail. The mixer channel is mounted to rotate about an axis parallel to the rail to mix samples and position the tubes to be aspirated. A push pin mounted adjacent to the mixer channel extends into the mixer channel and urges individual tubes against an aspirator assembly mounted on the opposite side of the mixer channel. An input queue is disposed proximate the input side of the rail and an output queue disposed proximate the output side of rail. The input queue supports the racks and feeds them into position to be driven by the car mechanism into the mixer channel. The output queue receives racks after being aspirated and feeds them aft to make room for subsequent racks driven by the car from the mixer channel. The racks include a lateral front wall, a lateral rear wall and a horizontal bottom wall connecting the front wall to the back wall. The racks also include a plurality of vertical side walls connected to the front wall and the back wall to define a plurality of tube receptacles. The bottom wall includes a plurality of equidistantly spaced apertures, each of which is centrally located within a tube receptacle to provide the push pin access to the tubes. The bottom wall also includes a plurality of ribs extending from the front wall to the back wall to be engaged by the car. Biasing means are disposed within each of the tube receptacles to support sample tubes therein.

16 Claims, 25 Drawing Sheets

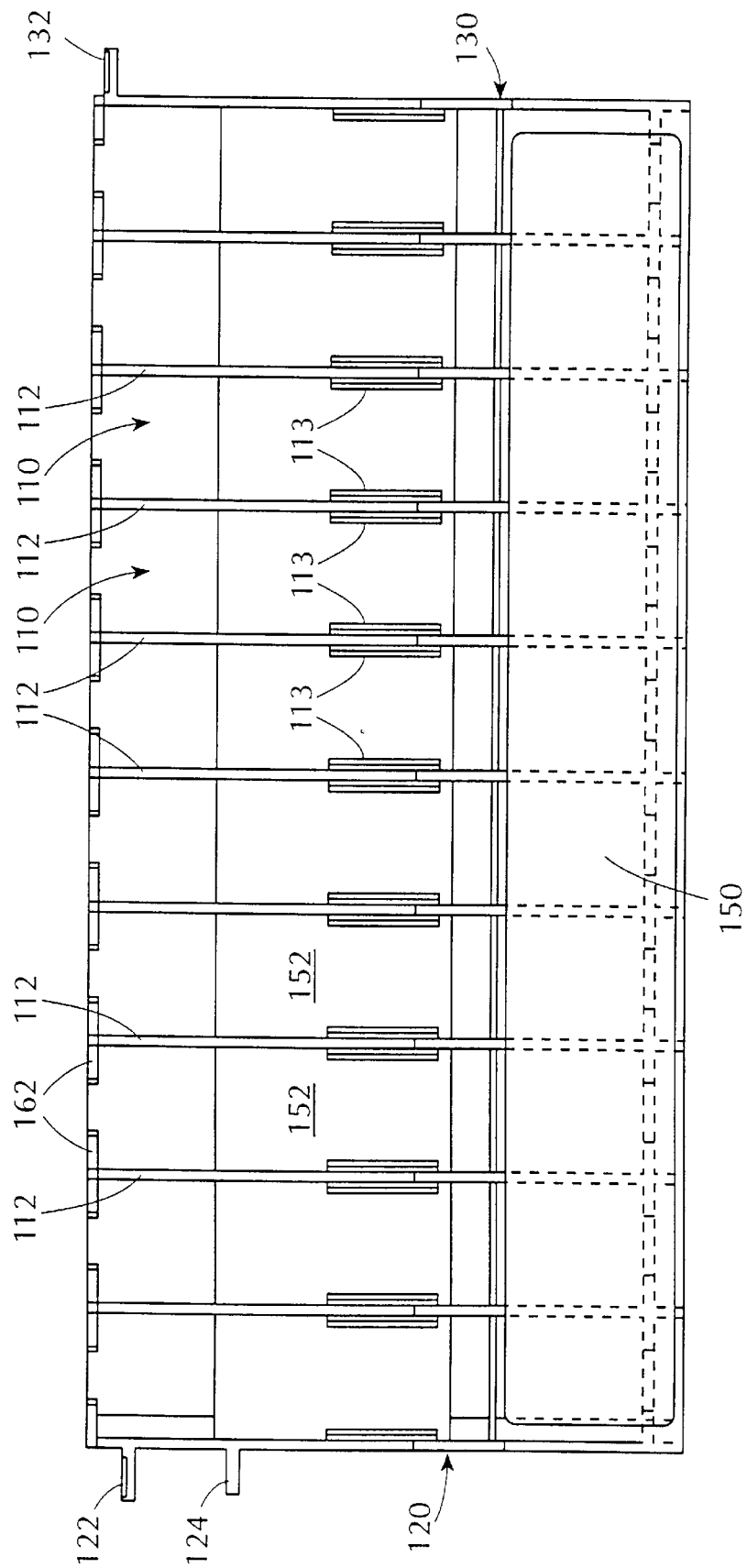

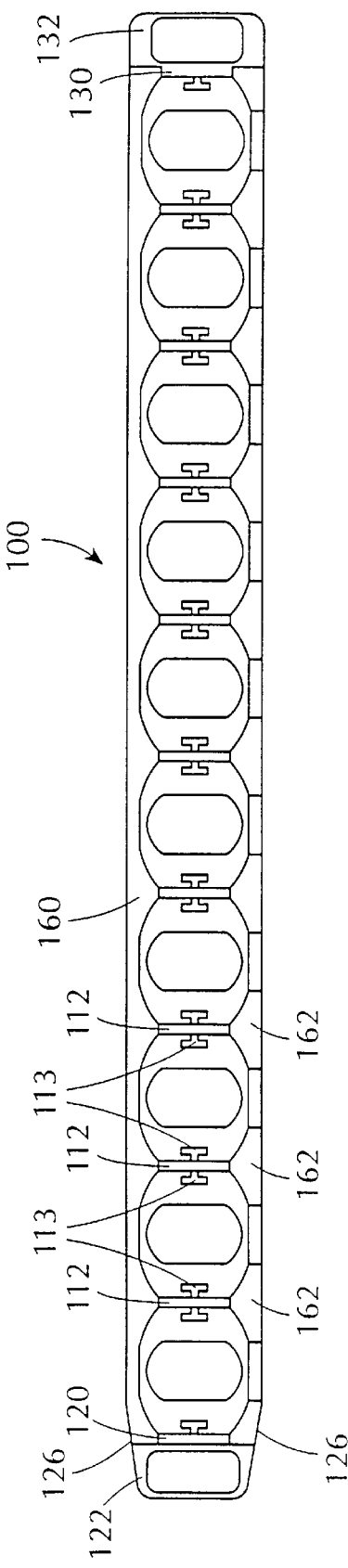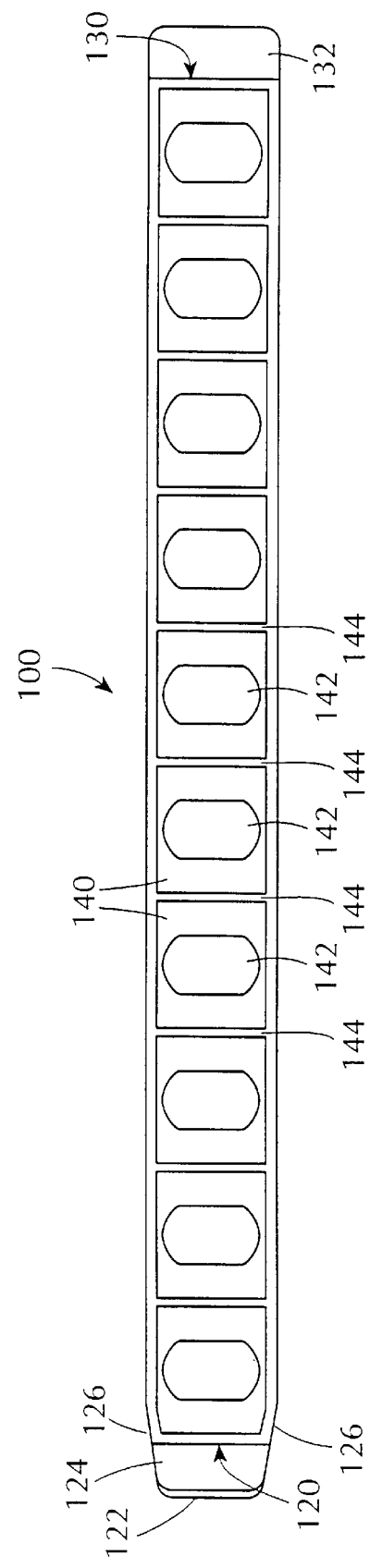

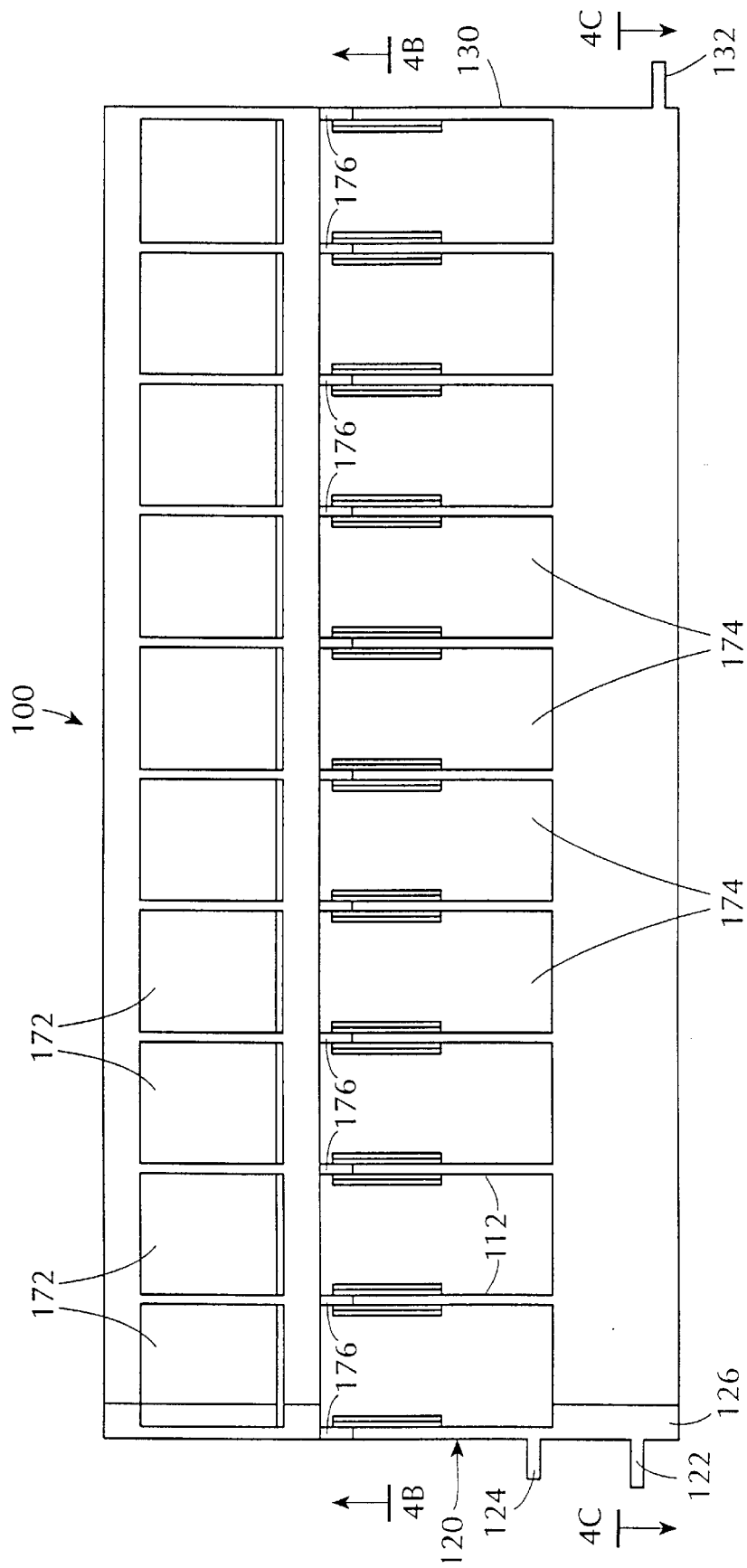

AUTOMATIC CLOSED TUBE SAMPLER

This is a divisional of application Ser. No. 08/822,585 filed on Mar. 20, 1997, now U.S. Pat. No. 5,861,563.

FIELD OF THE INVENTION

The present invention relates to a method and apparatus for automatically transporting, mixing and aspirating samples, such as blood, from multiple sealed containers.

BACKGROUND OF INVENTION

Blood is typically collected from patients in closed, evacuated sample tubes. The samples contained in these tubes are later aspirated from the tubes so that various tests may be performed. However, in order to obtain a substantially homogenous mixture for testing (e.g., an even distribution of blood cells) it is first necessary to mix the sample before aspiration. Further, because vigorous mixing may cause damage to delicate blood cells, a means for gently mixing the samples before aspiration is required.

One system for mixing and aspirating blood samples is disclosed in U.S. Pat. No. 4,331,484, wherein a pair of vertical screw-threaded shafts convey a series of closed containers downward towards a retractable aspiration needle. Differential speed of the feed screws imparts a gentle rocking and rotation on the tubes as they are transported towards the aspiration needle. The disclosed system is limited, however, in that sample tubes must be input individually and optimum mixing is not adequately accomplished. In addition, only tubes of like dimensions may be processed simultaneously. As various tube manufacturers produce sample tubes with different dimensions and sizes, it is desirable that an automated sampler be capable of dealing with sample tubes of varying characteristics simultaneously.

Another system, disclosed in U.S. Pat. No. 4,475,411, includes a vertically mounted, rotatable round cassette in which sample tubes are mounted along the periphery. The number of tubes is limited in this system by the size of the cassette. In addition, the cassette cannot be changed while samples are being aspirated.

U.S. Pat. No. 4,609,017 describes a system in which sample tubes are housed in racks, which are vertically stacked, with the tubes in their horizontal orientation, in an input compartment. The racks are stripped from the bottom of the stack one at a time by an input elevator and lowered onto a combined conveyor belt and tilt table. The tilt table mixes the tubes as the conveyor advances the racks to an aspiration station. The sample tubes are then individually indexed to an aspiration probe with the tilt table tilted so that the sealed tube end is below the opposite end. Once samples have been taken from every tube in the rack, the rack is advanced to an output elevator and stacked vertically in an output compartment.

The racks used in the above system are described in U.S. Pat. No. 4,534,465. Each rack includes a base, a front wall and an intermediate wall, wherein the intermediate wall is disposed approximately midway between the base and the front wall. The front wall and the intermediate wall include a linear series of aligned apertures for receiving sample tubes. A spring is disposed between the front wall and the intermediate wall for holding sample tubes against the upper edges of the apertures.

The system of the '017 patent (including the rack of the '465 patent) is limited, however, in the ability to add or remove racks from the input and output stacks. Because the racks are vertically stacked in the input and output compartments, the ability to add or remove racks from the middle of these stacks is precluded without first removing racks above the desired position.

SUMMARY OF THE INVENTION

It is, therefore, an object of the present invention to provide a system for automatically mixing sample tubes and aspirating a portion of each tube's contents for testing by an analyzer.

A further object of the present invention is to provide a mixer/aspirator system designed to simultaneously handle sample tubes of differing dimensions and volumes.

Still another object of the invention is to provide a rack to support sample tubes of differing dimensions and volumes.

The above and other objects are achieved in accordance with a first aspect of the invention by an apparatus for transporting racks of sealed sample tubes, mixing a sample material contained within the tubes, and aspirating samples from the tubes. The apparatus includes a car which runs along a rail. The car drives racks containing the sample tubes into a mixer channel disposed above and running parallel to the rail. The mixer channel is mounted to rotate about an axis parallel to the rail to mix samples and position the tubes to be aspirated. A push pin mounted adjacent to the mixer channel extends into the mixer channel and urges individual tubes against an aspirator assembly mounted on the opposite side of the mixer channel. An input queue is disposed proximate the input side of the rail and an output queue disposed proximate the output side of rail. The input queue supports the racks and feeds them into position to be driven by the car mechanism into the mixer channel. The output queue receives racks after being aspirated.

In another aspect of the present invention racks are provided which include a lateral front wall, a lateral rear wall and a horizontal bottom wall connecting the front wall to the back wall. The racks also include a plurality of vertical side walls connected to the front wall and the back wall to define a plurality of tube receptacles. The bottom wall includes a plurality of equidistantly spaced apertures, each of which is centrally located within a tube receptacle to provide the push pin access to the tubes. The bottom wall also includes a plurality of ribs extending from the front wall to the back wall to be engaged by the car. Biasing means are disposed within each of the tube receptacles to support sample tubes therein.

These and other objects, features and advantages of the present invention will be apparent and fully understood from the following detailed description of the preferred embodiments, taken in connection with the appended drawings.

BRIEF DESCRIPTION OF THE DRAWINGS

The present invention can be better understood when considered with the following drawings wherein:

FIG. 3A is a front elevational view of the rack of FIG. 2;

FIG. 3B is a top plan view of the rack of FIG. 2;

FIG. 3C is a bottom view of the rack of FIG. 2;

FIG. 4A is a rear elevational view of the rack of FIG. 2;

DETAILED DESCRIPTION OF THE PREFERRED EMBODIMENT

Figure 1:
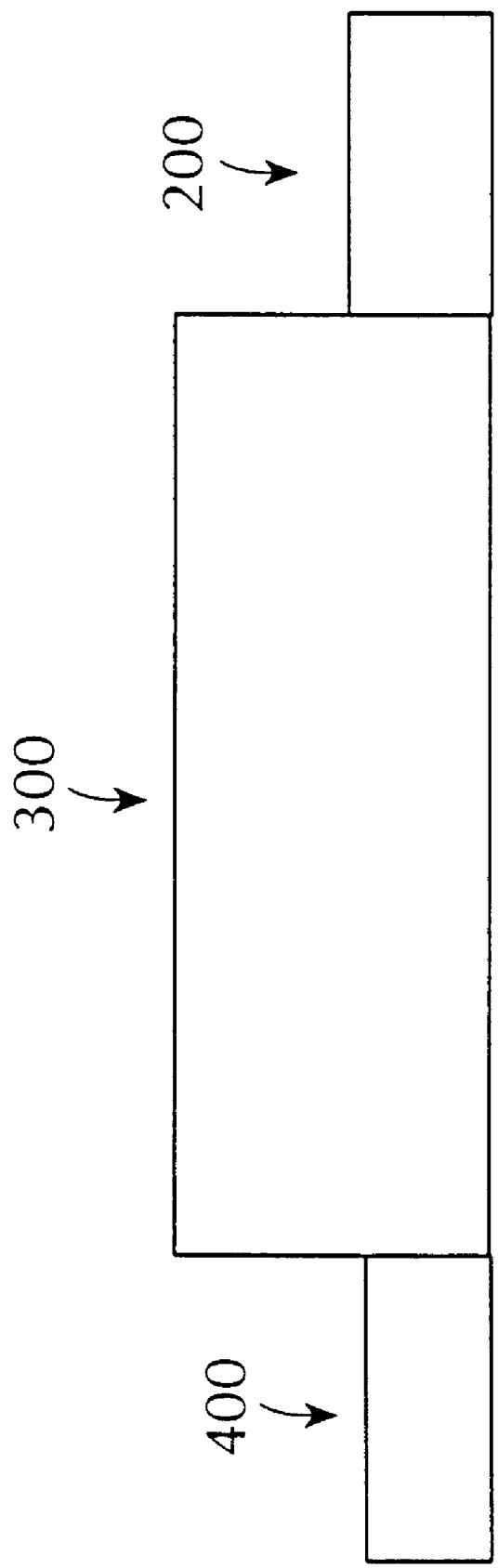
FIG. 1 is a schematic diagram of the Automatic Closed Tube Sampler of the present invention.
Figure 2:
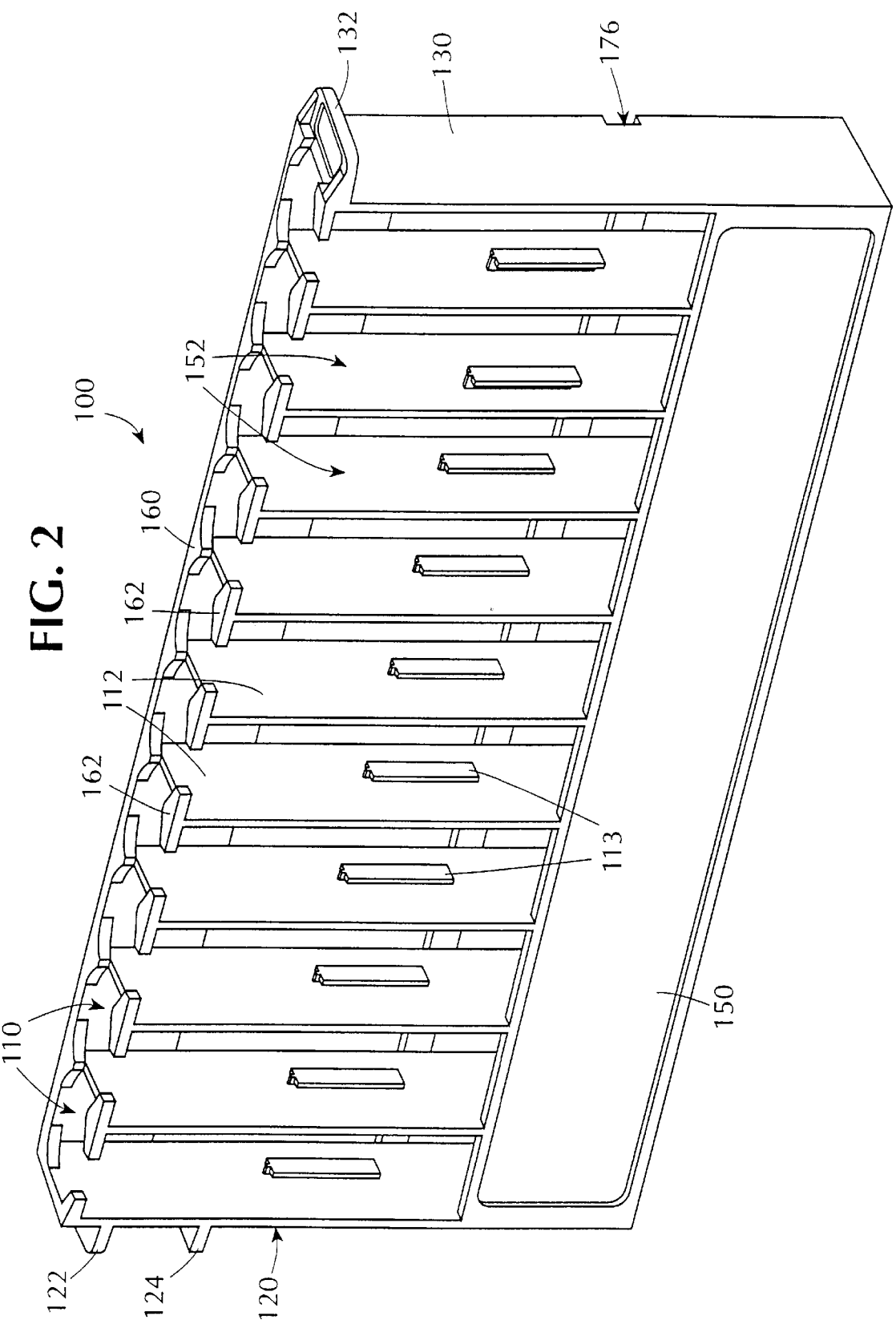
FIG. 2 is a perspective view of a rack used in the Automatic Closed Tube Sampler of the present invention.
Figure 4B:
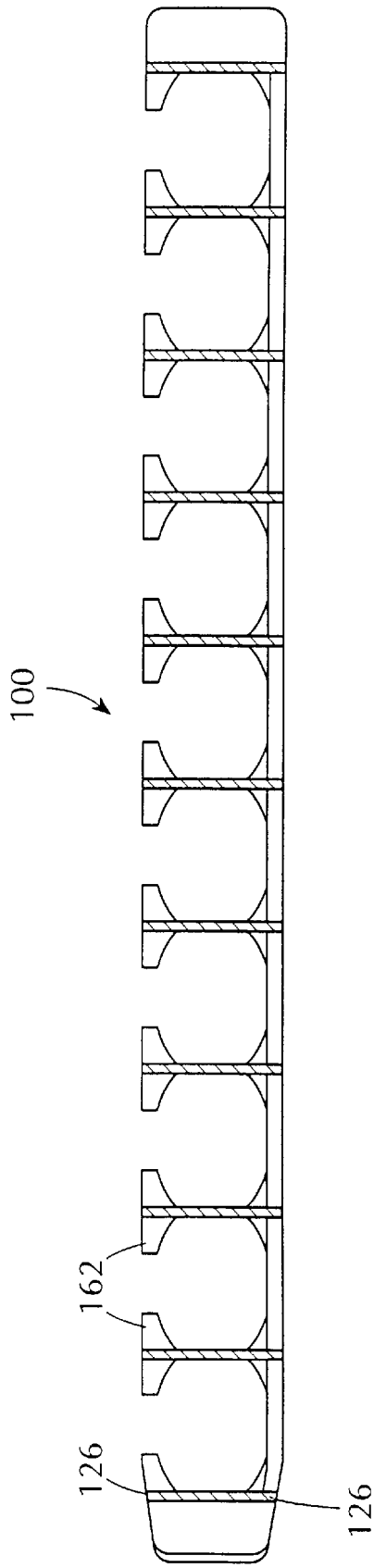
FIG. 4B is a cross-sectional view of the rack of FIG. 2 taken along line A—A in FIG. 4A.
Figure 4C:
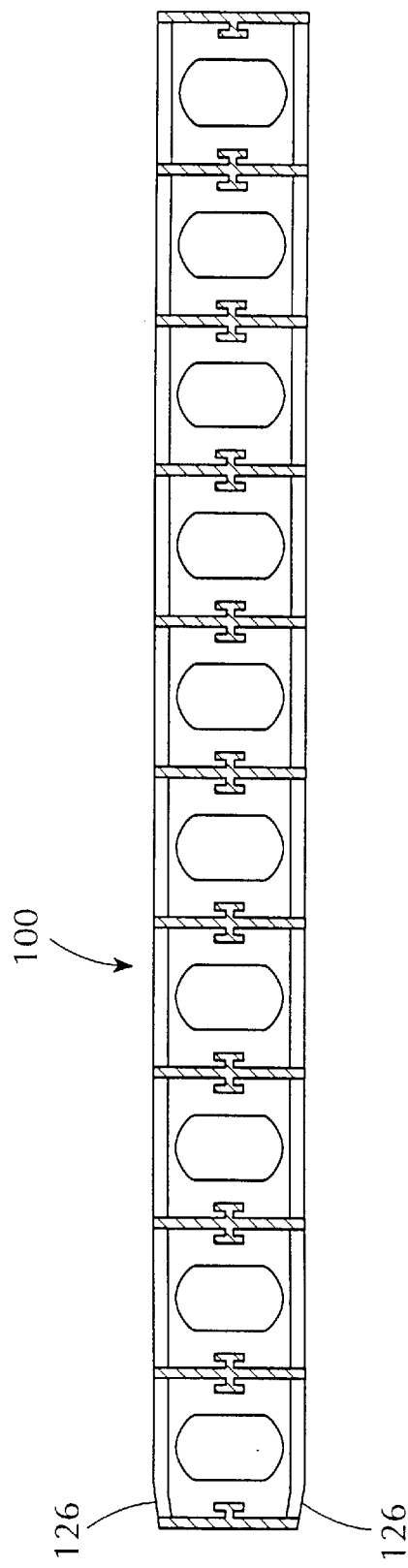
FIG. 4C is a cross-sectional view of the rack of FIG. 2 taken along line B—B in FIG. 4A.

Referring to FIG. 1, the automatic closed tube sampler 1 (hereinafter "autosampler") of the present invention includes three main sections; the input section 200, the mixer/aspirator section 300 and the output section 400. Tubes containing samples to be aspirated are held in racks 100 and transported between the above sections by a car mechanism 500 traveling on a rail 550. Each of these components is described in detail below.

The Racks

Referring to FIGS. 2–4C, the autosampler of the present invention uses plastic racks 100 to hold sample tubes and transport them through the autosampler. The racks 100 of the preferred embodiment are injection molded out of a plastic which is chemically compatible with the cleaning agents used in the laboratory environment, e.g., ABS plastic.

Each rack 100 holds a series of tubes in individual receptacles 110 formed in a single row in the rack 100. The receptacles 110 are defined by vertical side walls 112 which divide the rack into individual tube receptacles 110. The rack of the preferred embodiment includes eleven vertical side walls 112 thereby defining ten tube receptacles 110 to hold up to ten sample tubes.

Mounted on both ends 120 and 130 of the rack 100 near the top are "ears" 122, 124 and 132. There are two ears 122, 124 on end 120 to distinguish it from end 130 which has only one ear 132. This second ear 122 on end 120 also provides a convenient location for labels and provides an easily accessible place for an operator to hold and pick-up the rack 100.

The racks 100 hang from ears 124 and 132 in the input and output queues. The ear 124 mounted on end 120 is disposed further from the top of the rack than ear 132 on end 130 to ensure the racks 100 are loaded in the queues in the proper orientation, as more fully described below. The racks 100 also incorporate chamfered portions 126 on their left, i.e., leading end 120 (FIGS. 3B and 3C) to facilitate transfer through the aspirator/mixer section 300 to the output section 400, in particular, through the mixer channel 310, as described below.

Formed along the bottom of each rack 100 is a bottom wall 140, best seen in FIG. 3C. The bottom wall 140 includes an aperture 142 disposed vertically below each of the tube receptacles 110 to provide access for the tube push pin 392. As described in detail below, the tube push pin 392 is used in the aspirator/mixer section 300 to urge the tubes towards the aspirator mechanism 600. The bottom wall 140 also includes ribs 144 formed on its outer surface extending from the front of the rack towards the back. The ribs 144 are located vertically below the side walls 112, i.e., between each tube receptacle 110 and under the ends 120 and 130 of the rack 100. These ribs 144 interface with the car drive pawl 510 (described below) to translate the rack 100 laterally from the input section 200, through the mixer/aspirator section 300, to the output section 400.

The front of each rack 100 includes a front wall 150 formed across the width of the rack 100 and covering approximately the bottom third of the side walls 112. See, FIG. 3A. This front wall 150 provides a convenient location to affix labels containing identifying indicia. For example, in the preferred embodiment, an ID label encodes the rack number and tube position number at each tube receptacle 110 in a machine-readable format (e.g., barcode).

The top surface 160 of the rack 100 includes projections 162 formed at the front end of each side wall 112. These projections 162, best seen in FIGS. 2, 3A, 3B and 4B, help guide the tubes into the rack 100 when being loaded by an operator. Human-readable tube position numbers are molded in the top surface 160 of the rack 100 at each tube receptacle 110, for example, on projections 162 (FIG. 3B). These numbers, along with labels containing the rack ID which are affixed to the ears 122 and 132, provide a human-readable identification corresponding to the machine readable identification previously described.

Label windows 152 are formed in the front of the rack 100 adjacent to each sample tube receptacle 110. These label windows 152 provide access to tube labels so that they may be read by the autosampler without removing the tubes from the rack 100. The operator is responsible for installing sample tubes correctly in the rack 100 so that the tube labels are visible through the windows 152. In the preferred embodiment, the height of the rack barcode label is 23 mm and the size of each sample tube label window 152 in the rack 100 is a minimum of 63 mm long by approximately 9 mm wide.

Each rack 100 includes a back wall 170, shown in FIG. 4A, across the back of the rack 100. In a preferred embodiment, this back wall 170 includes apertures 172 and 174 at each tube receptacle, however, these apertures are not material to the functionality of the rack 100. Also formed across the entire width of the back of rack 100 is a horizontal groove 176 which is used to retain the rack 100 in the mixer channel 310, as described in detail below. In the illustrated embodiment, this groove 176 is formed in the rear of each side wall 112 and end walls 120 and 130. (See FIG. 2).

Figure 5A:
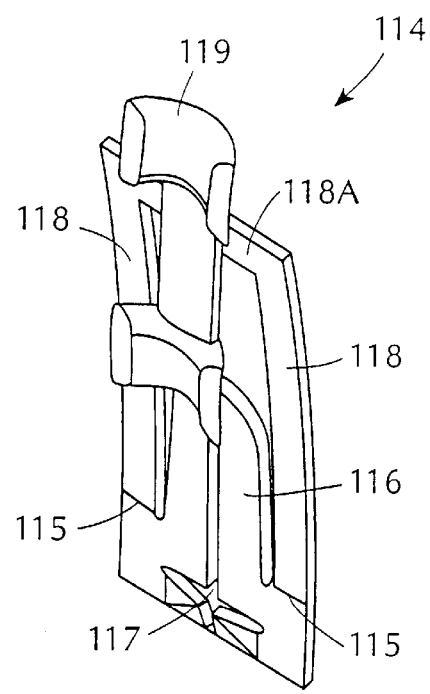
FIG. 5A is a perspective view of the leaf spring used in the rack of FIG. 2.
Figure 5B:
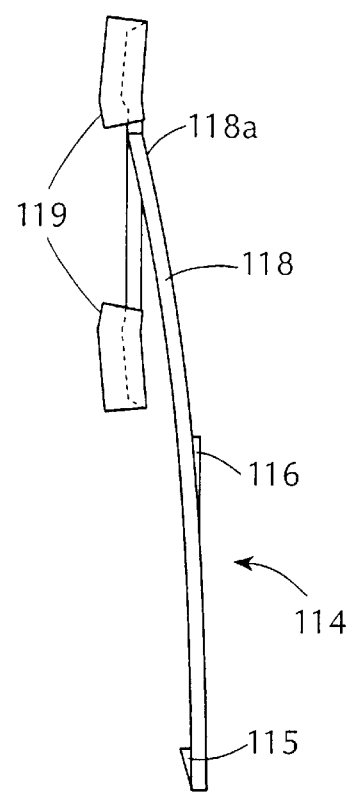
FIG. 5B is a front elevational view of the leaf spring of FIG. 5A.
Figure 5C:
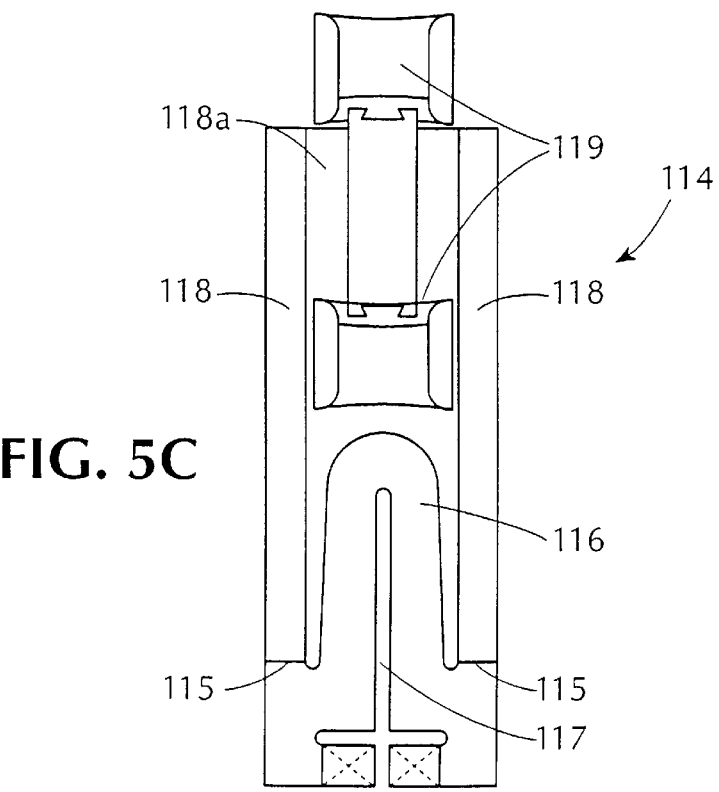
FIG. 5C is a side elevational view of the leaf spring of FIG. 5A.

Located within each tube receptacle 110 are two leaf springs 114, one mounted to each side wall 112 opposite each other at approximately the vertical midpoint of the tube receptacle 110. As shown in FIGS. 5A–5C, each leaf spring 114 includes an inner U-shaped portion 116 and a larger, outer U-shaped portion 118. Portion 116 is mounted to the side wall 112 and portion 118 is angled away from the plane containing portion. 116, thereby extending into the tube receptacle to engage the tube. The two U-shaped portions 116, 118 are connected at a point 115 proximate their ends.

In the illustrated embodiment, the portion 116 is mounted to the wall 112 by way of a slot 117 formed vertically through its center. This slot 117 engages a spring tab 113 formed in the side wall 112 (FIGS. 2, 3A and 3B) to secure the leaf spring 114 to the wall 112. The middle section 118a of portion 118 includes an arcuate member 119 for engaging the outer surface of a sample tube. These springs 114 provide support to a tube contained within the receptacle 110 and hold the tube within the rack 100.

Because these springs 114 are mounted on both sides of each tube receptacle 110 at approximately the vertical mid point, the racks 100 are capable of accommodating tubes of varying sizes. For example, the racks 100 of the preferred embodiment have been found suitable for sample tubes with nominal diameters between 10 and 13 mm, in nominal lengths ranging from 50–65 mm for the 10 mm tubes and from 75–100 mm for the 13 mm tubes. The springs 114 also center all sizes of tubes to the same center line since there is one spring 114 on each side of every tube.

In operation, an operator loads the racks 100 with sample tubes approved for use. The tubes must be inserted far enough into the rack 100 so that the rack 100 and tubes don't exceed the height of the inside of the mixer channel 310. If barcode labels are present on the tubes, the operator must orient the tubes so that the barcode symbol appears in the window 152 provided in the rack 100. It is recommended that the top of the label start at the top of the tube just under the bottom of the cap or lip. It should be understood, however, that tube labels are convenient, but not required for autosampler operation as individual tube identification is provide by rack and receptacle numbers.

The Input Section

Referring to FIG. 1, the input section 200 is located to the right of the mixer/aspirator section 300, outside the autosampler's mixer/aspirator enclosure. The input section 200, illustrated in FIGS. 6A–8, includes an input queue 210 and an input shuttle 250 formed in the cover 204 of the input section 200. In the preferred embodiment, the input section 200 holds up to fifteen racks 100 of sample tubes, including one rack in the input shuttle 250, in anticipation of their being processed by the autosampler.

The input queue 210 is essentially an open topped box having a front wall 212, a rear wall 214, two side walls 216 and 218 and a bottom 220. The top edges of the side walls 216 and 218 form a pair of stationary guide rails 217 and 219, respectively. The racks 100 are supported in the input queue 210 by their ears 124 and 132, which rest on the stationary guide rails 217 and 219 and hold the racks 100 suspended within the input queue 210.

The guide rails 217 and 219 are disposed at two different heights to correspond to the location of the ears 124 and 132 on sides 120 and 130 of the racks 100 so that the racks 100 will be held level when loaded properly. This feature is particularly useful to ensure that the operator loads racks 100 in the proper orientation, e.g., so that the autosampler read the barcodes. If a rack 100 is loaded in the reverse orientation by mistake the rack 100 will not sit level in the queue 210, giving a visual indication of the error.

The input shuttle 250 is the front-most part of the input queue 210, where racks 100 stop at the end of their forward travel (induced by the input queue feed mechanism described below) and from which they are driven by the car mechanism 500 (not shown in FIGS. 6A–8 ) into the mixer/aspirator section 300. If the input shuttle 250 is empty the user can load a rack 100 there directly. In addition, the user can slide racks freely forward or backward in the queue 210 to accommodate any loading scenario. The user can also push racks towards the rear of the input queue 210 to clear the shuttle position 250. This allows placement of a "stat rack" before other racks in the queue 210.

Figure 6A:
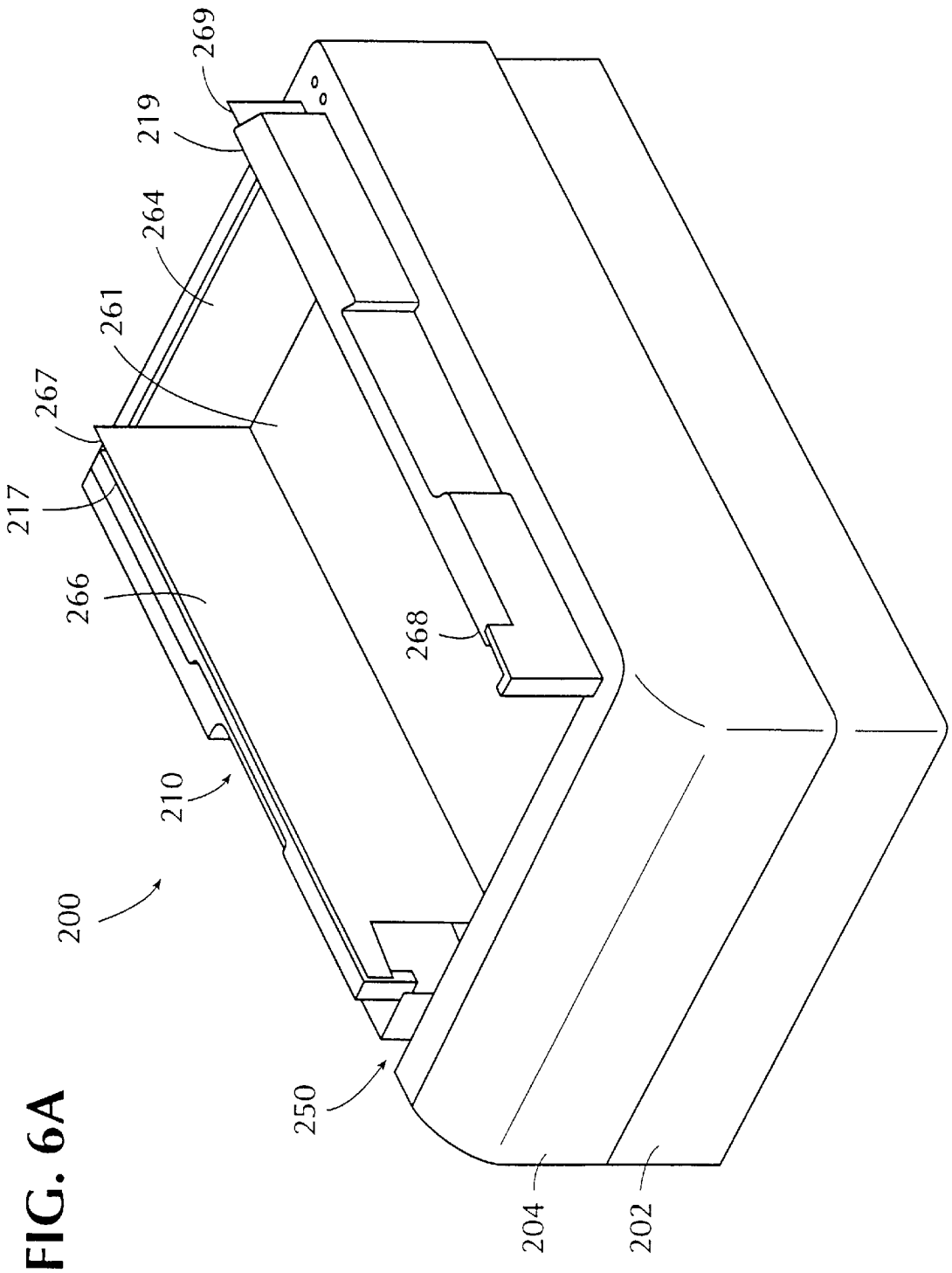
FIG. 6A is a perspective view of the input section of the present invention.
Figure 6B:
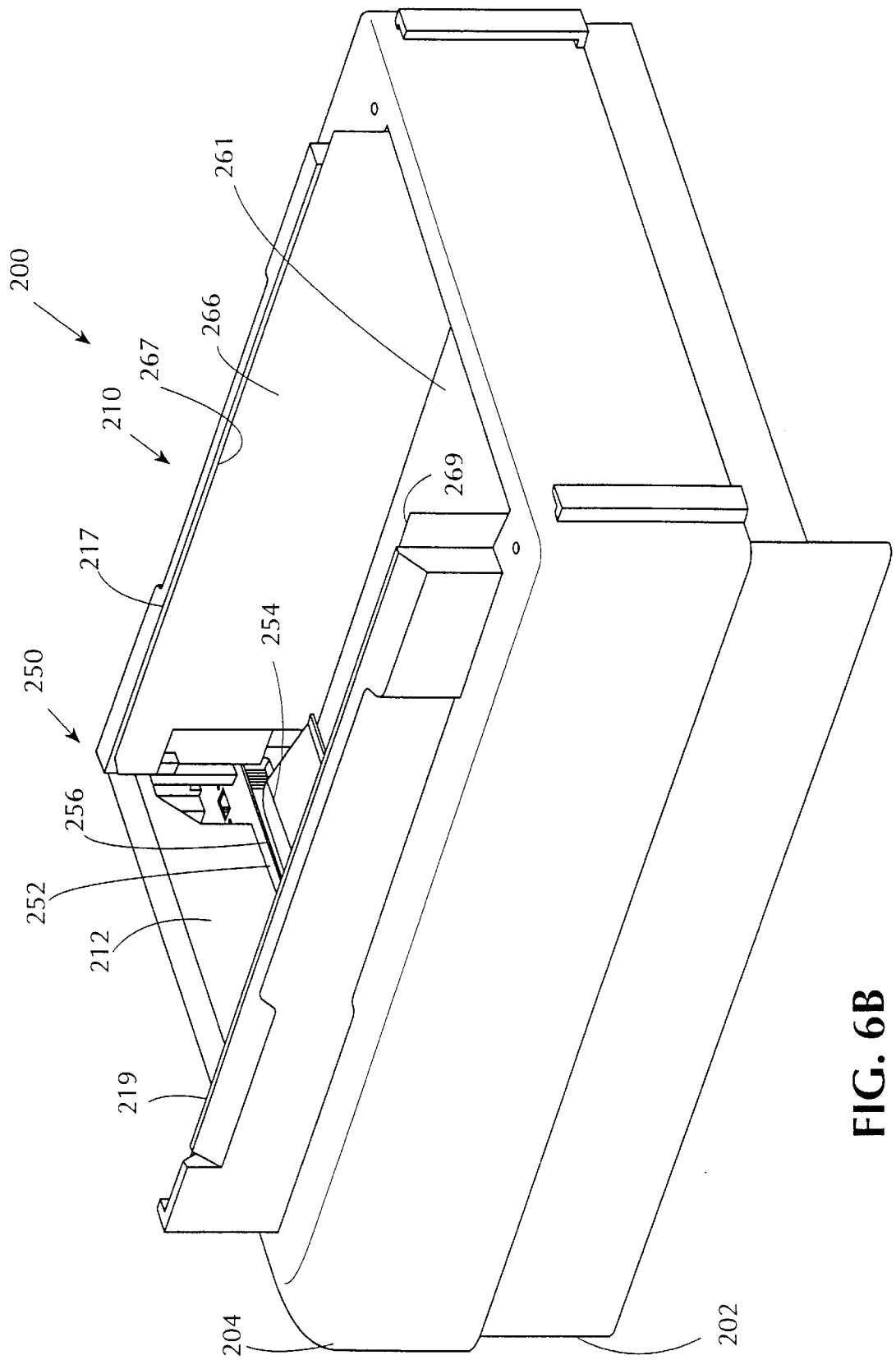
FIG. 6B is a perspective view of the input section of FIG. 6A viewed from a different angle.

As best seen in FIG. 6B, the input shuttle bed 252 is raised slightly with respect to the input queue bottom 220 so that the bottom of a rack 100 disposed in the input shuttle 250 sits on the shuttle bed 252 rather than on the stationary guide rails. The rack in the input shuttle is, therefore, disposed at an elevation just slightly higher than the racks 100 resting by their ears 124 and 132 on the stationary guide rails 217 and 219 in the input queue 210. While sitting in the input shuttle 250, a rack 100 is prevented from tipping forward by front wall 212. Should the rack 100 start to tip backward, ears 124 and 132 engage the stationary guide rails 217 and 219 to prevent it from tipping completely over.

The input queue section 210 is open at the front and the input shuttle 250 is open at the back, so that racks 100 can pass freely from the queue section 210 to shuttle 250, except that they must be raised a little to clear the lip 254 of the shuttle bed 252. The shuttle bed 252 also includes a lateral slot 256 (shown in FIG. 6B) on the side closest to the mixer/aspirator section 300. This slot 256 provides access for the car drive pawl 510 to a rack 100 in the input shuttle 250 so that the rack 100 may be drawn from the input shuttle 250 to the mixer/aspirator section 300, as described below.

The input shuttle 250 may also be provided with a movable door (not shown in the drawings) to prevent a rack 100 in the shuttle 250 from moving toward the mixer/aspirator section 300 far enough to cause the leading edge of the moving rail 267 to crash into the rack body during queue feed motion (described below). In one embodiment, the shuttle door is biased closed by a spring or the like to a normally closed position and is pushed open by the car 500 as it drives the rack 100 into the mixer/aspirator section 300. Alternatively, a mechanized door may be operated by pneumatic or similar means to controllably open and close the door when so desired.

The input shuttle 250 of the illustrated embodiment includes an input shuttle full sensor, which is preferably an optical sensor, to detect the presence and correct positioning of a rack 100 in the input shuttle 250. The sensor is located laterally in the middle of the rack 100 and is positioned to detect the bottom of the rack front wall 150 so that excessive rotation of the rack 100 around the longitudinal axis does not falsely indicate that the rack is in position for shuttling.

The input queue feed mechanism is comprised of a pair of walking beams driven by a motor, preferably a single DC gear motor, which feeds racks 100 in the forward direction to the input shuttle 250. In operation, a pair of moving rails 267 and 269 lift the racks 100 by their ears 124 and 132 from the stationary guide rails 217 and 219, translate them forward a fixed distance toward the shuttle 250 and set them down again on the stationary guide rails 217 and 219. A rack disposed in the foremost input queue position is simultaneously translated forward and set down in the input shuttle 250 where it rests on its base to await transport into the mixer/aspirator section 300.

In the illustrated embodiment, an input queue pan 260 having a rear wall 264, two side walls 266 and 268 and a bottom 261 is disposed within the input queue 210. The dimensions of the input queue pan 260 are such that it conforms to the size and shape of the input queue 210 and the top edges of the queue pan side walls 266 and 268 form the moving rails 267 and 269, respectively. When in their lowered position, the moving rails 267 and 269 are disposed just below the height of the corresponding stationary rails 217 and 219, thereby allowing the racks 100 to rest on the stationary rails 217 and 219, as previously described. The input queue pan 260 does not include a front wall, but rather a front lip 262. The front lip is formed to a height such that it does not impede the forward travel of racks 100, while at the same time containing any spillage.

Figure 8:
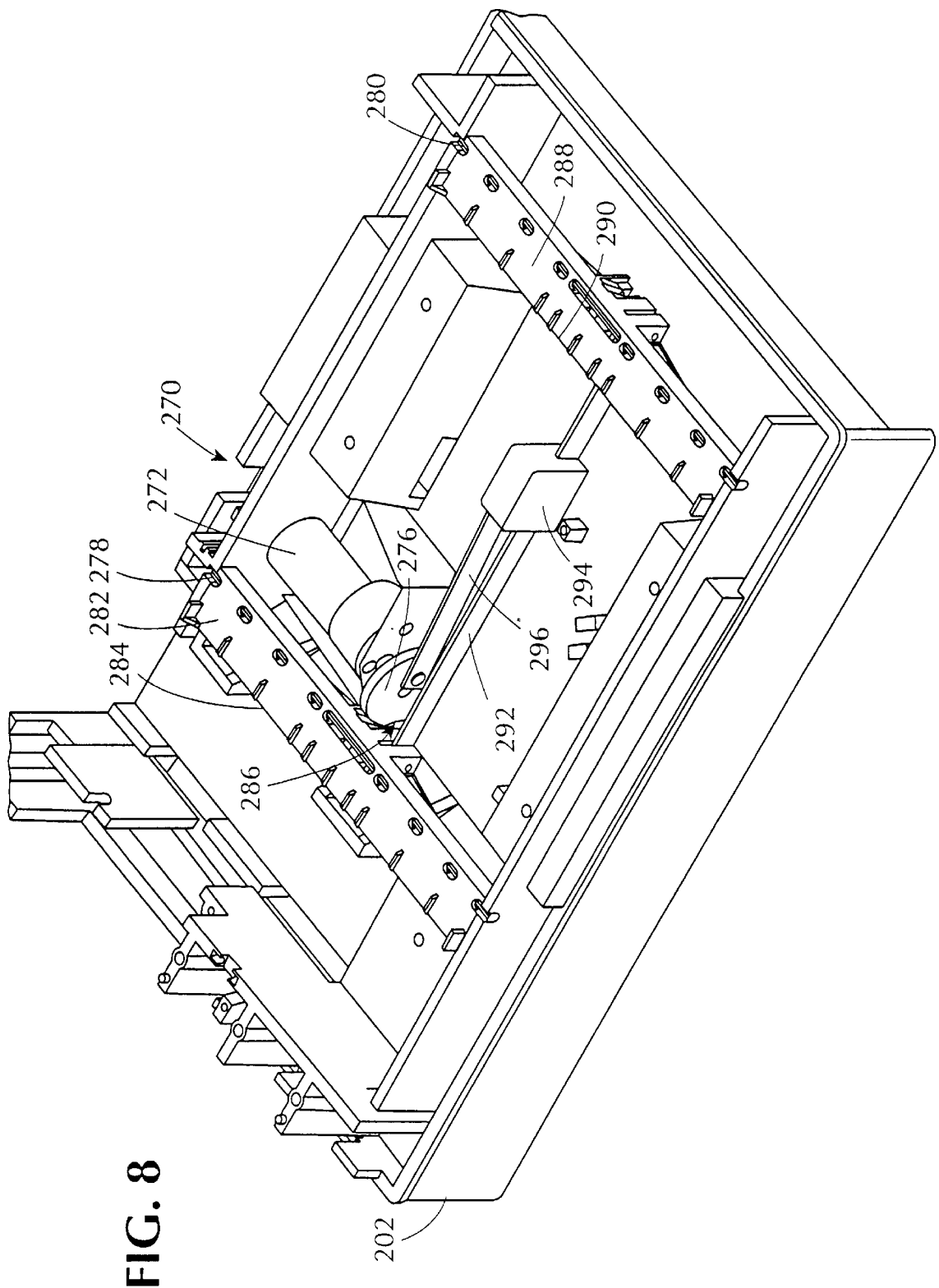
FIG. 8 is a perspective view of the walking beam drive mechanism of the input section of FIG. 6A viewed from the same angle as FIG. 6B.

The walking beam drive mechanism 270 is shown in FIG. 8, which shows the input section 200 with the input queue pan 260 and the input queue cover 204 removed. A pair of lift bars 282 and 288 are mounted to the base 202 of the input section 200, one bar 282 at the front of the input section and the other bar 288 at the rear, by respective rods 278 and 280. The drive motor 272 is mounted proximate the front lift bar 282 and includes a variable profile cam 276 mounted to its drive shaft. A roller 286 is mounted to the front lift bar 282 below the pivot axis of the lift bar 282 about the rod 278, adjacent to the cam 276. When the roller 286 encounters the cam 276, the roller 286 is urged forward, causing the lift bar 282 to pivot about the rod 278 and the forward edge 284 of the lift bar 282 to raise vertically.

Figure 7:
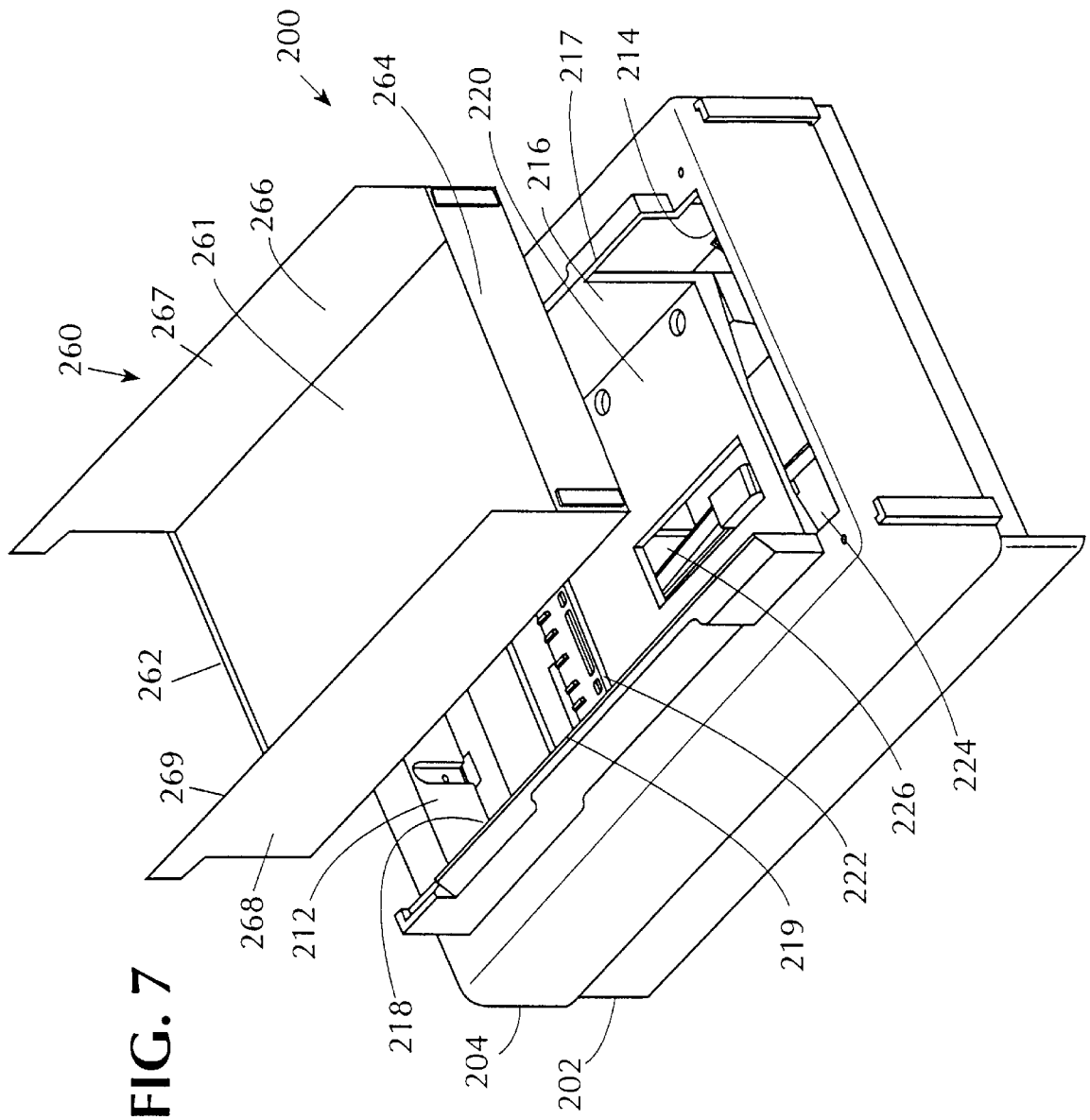
FIG. 7 is a partially exploded perspective view of the input section of FIG. 6A viewed from the same angle as FIG. 6B.

The rear lift bar 288 is connected to the front lift bar 282 by a tie rod 292. The tie rod 292 is mounted to the front lift bar 282 adjacent the roller 286 and is mounted to the rear lift bar 288 at a corresponding location, thereby driving the rear lift bar 288 in synchronization with the front lift bar 282. When the input section 200 is completely assembled (FIGS. 6A and 6 B), the queue pan 260 rests on top of the lift bars 282 and 288, which extend into the input queue at apertures 222 and 224 (FIG. 7).

Referring back to FIG. 8, a slider block 294 is connected to the cam 276 by a connecting rod 296 and is disposed on the tie rod 292 to slide along its length. The connecting rod 296 is connected to the cam 276 at a location such that the slider block 294 is driven forward when the lift bars 282 and 288 are raised and is driven back when the lift bars 282 and 288 are lowered. The slider block 294 engages a feature on the bottom of the queue pan 260 through another aperture 226 in the input queue 210.

In operation, racks 100 with sample tubes are loaded into the input queue 210, with the ears 124 and 132 resting on the stationary rails 217 and 219, respectively. When the motor 272 is activated, the cam 276 is rotated, urging the roller 286 forward and causing the lift bars 282 and 288 to pivot about the rods 278 and 280. This raises the front edges 284 and 290 of the lift bars 282 and 288, which in turn raise the queue pan 260. Consequently, the moving rails 267 and 269 are raised to a height above the stationary rails 217 and 219 and the racks 100 are picked-up off of the stationary rails 217 and 219 to be supported by the moving rails 267 and 269. The slider block 294 then urges the queue pan 260 (and hence the moving rails 267 and 269 ) forward, moving the racks 100 forward in the input queue 210. At the end of forward travel, the cam 276 ceases to urge the roller 286 forward and the lift bars 282 and 288 are lowered, thereby lowering the queue pan 260 and depositing the racks 100 on the stationary rails 217 and 219. The queue pan 260 is then moved rearward to the starting position by the slider block 294.

To fill the input shuttle 250 the input queue feed motor 272 is enabled for a time dependent on the initial location of the rack nearest the shuttle 250 in the input queue 210. The queue feed mechanism runs for a number of cycles until a rack 100 fills the shuttle 250 or until the maximum number of cycles is reached. The maximum number of cycles is equal to the maximum number of racks 100 that can fit in the input queue 210 since a single rack 100 located at the back of the input queue 210 must be allowed to reach the shuttle 250. An input queue empty/jam condition is detected when the input shuttle full sensor output is false after the maximum number of input queue feed cycles have transpired. This condition may be indicated to an operator by an appropriate alarm, which may be visual or audible.

The Car and Rail Assembly

Once a rack 100 has been loaded into the input shuttle 250, a car mechanism 500 running along a rail assembly 550 drives the loaded rack 100 from the input shuttle 250 through the mixer/aspirator section 300 to the output shuttle 450 in stages: input shuttle 250 to mixer 310, index to aspirator 600 (once for each tube position; ten times in all), aspirator 600 to staging area 364, staging area 364 to output shuttle 450.

Figure 9:
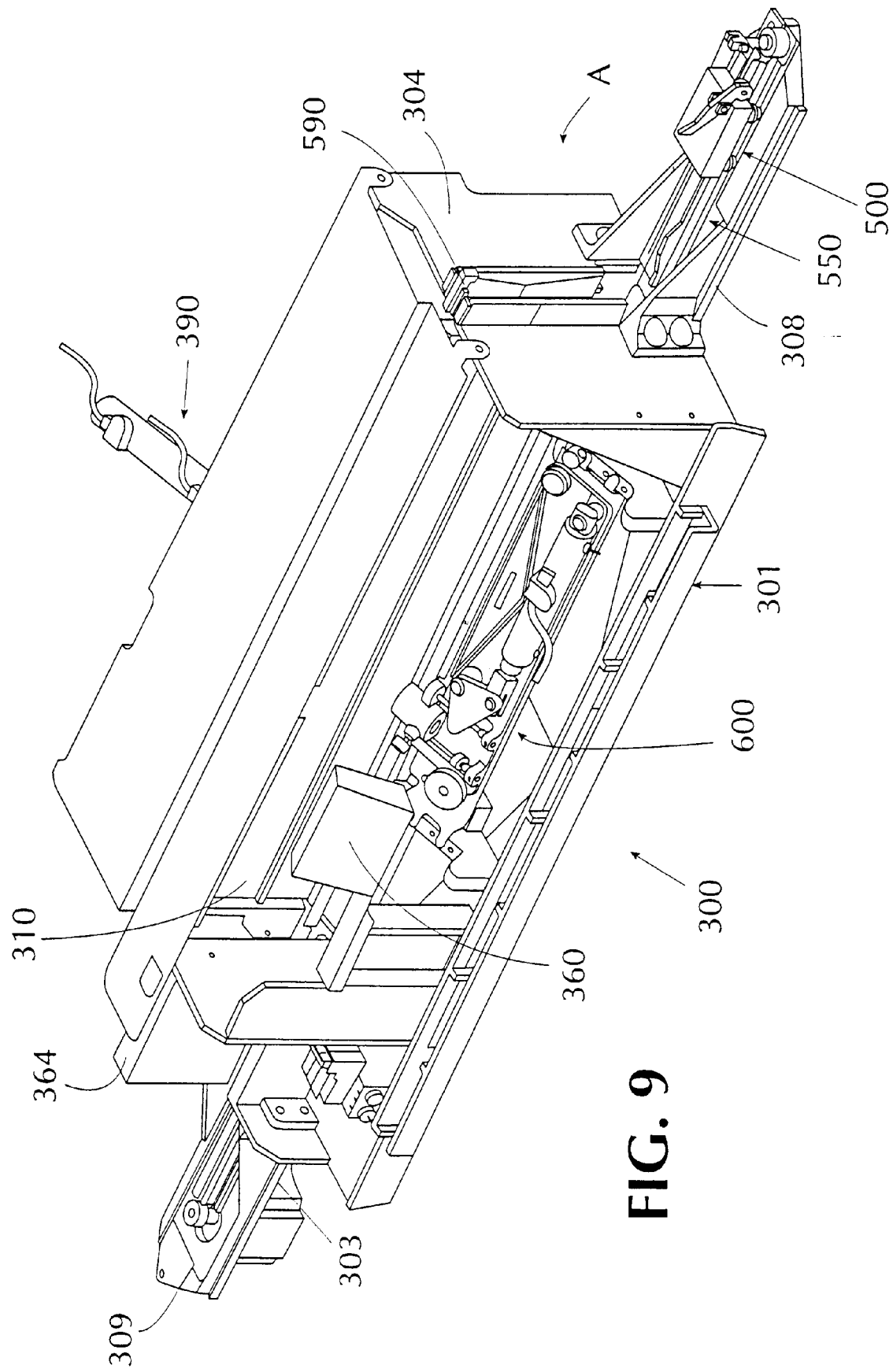
FIG. 9 is a perspective view of the mixer/aspirator section of the present invention depicted with the car and rail assembly.
Figure 12:
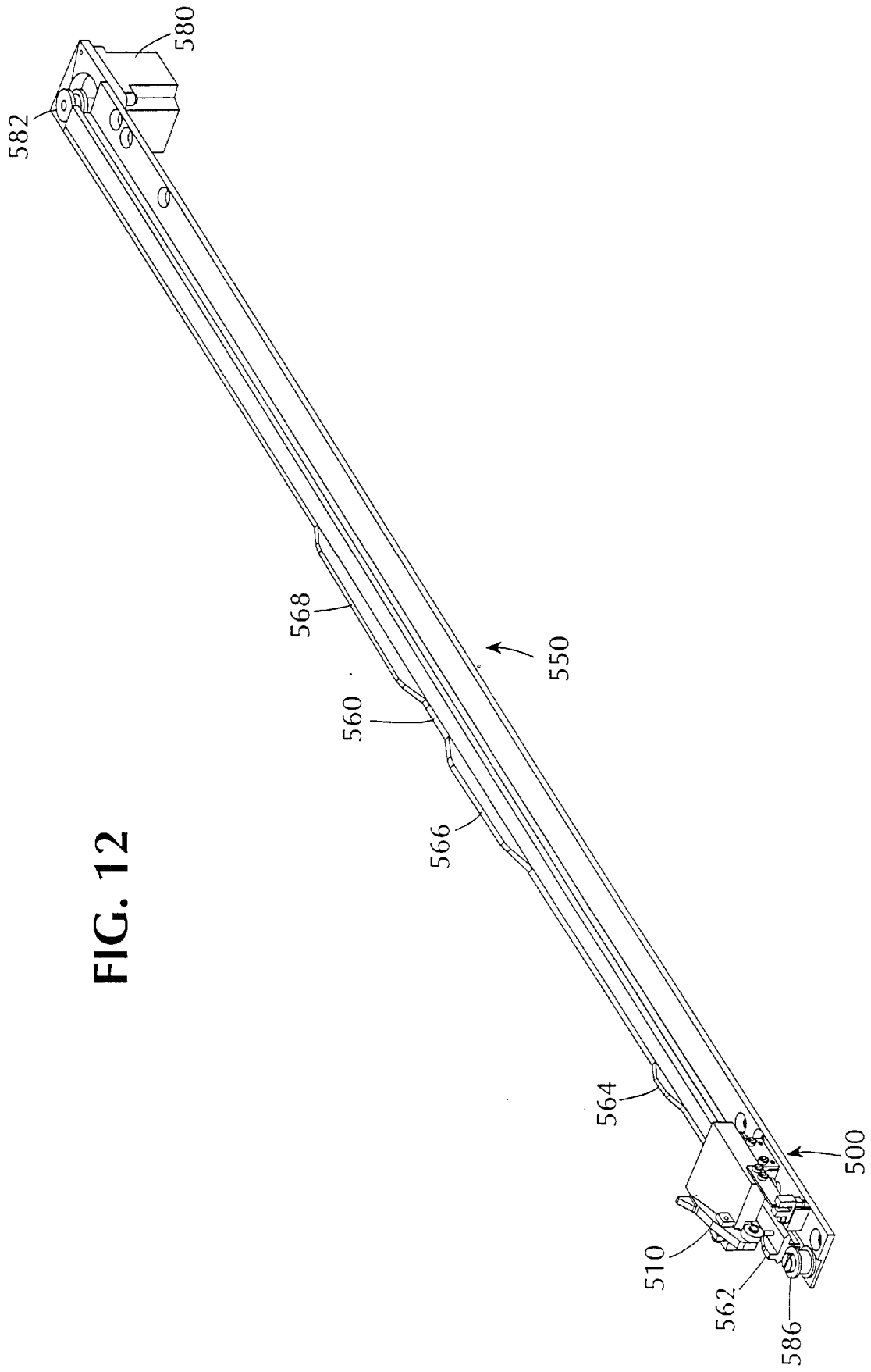
FIG. 12 is a perspective view of the car and rail assembly of the present invention.

FIG. 9 shows the car 500 and rail assembly 550 with respect to the mixer/aspirator section 300. For clarity, the input section 200 and the output section 400 have been removed. FIG. 12 shows a reverse perspective view of the car 500 and rail assembly 550 with the mixer/aspirator section 300 removed as well.

Figure 13:
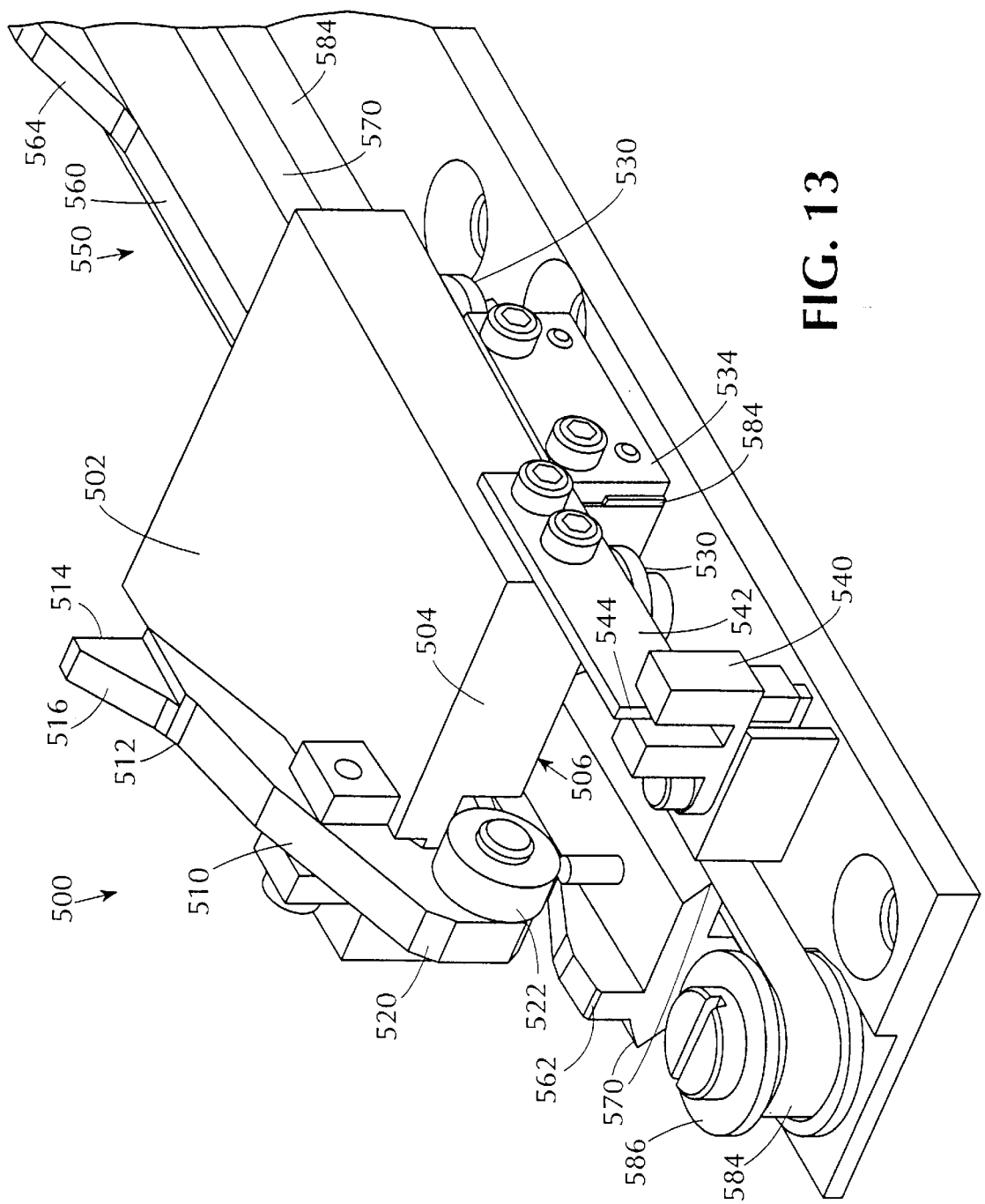
FIG. 13 is a perspective view of the car mechanism of the present invention.
Figure 14:
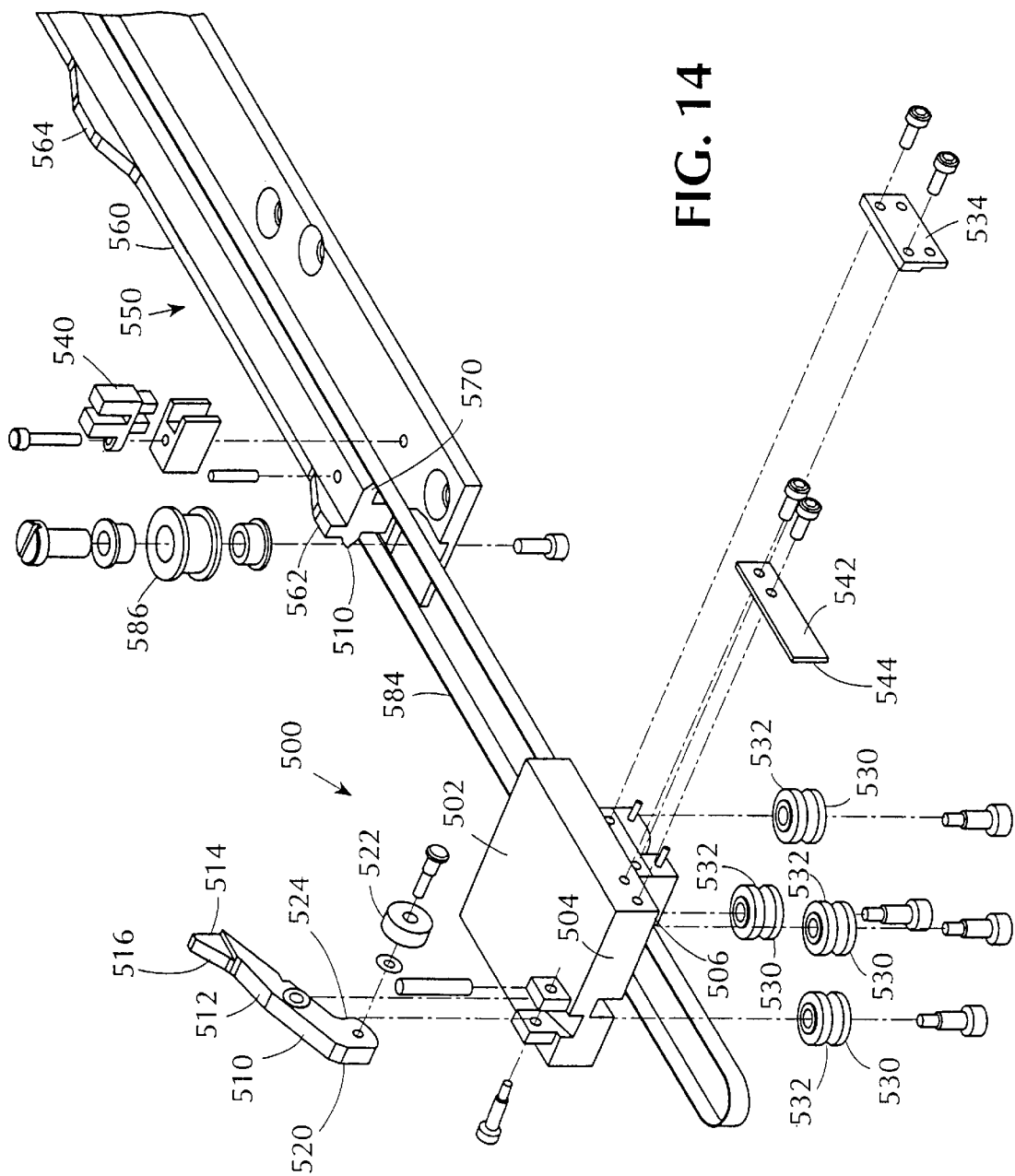
FIG. 14 is an exploded perspective view of the car mechanism of FIG. 13.

Referring to FIGS. 13 and 14, the car 500 includes a spring-loaded drive pawl 510 which is pivotally mounted to the top 502 of the car 500 near its right (i.e., input) side 504. The drive pawl 510 is pivotally mounted to the car 500 at about the pawl's mid point, with one arm 512 extending up and to the left, and the other arm 520 extending down and to the right along the right side 504 of the car 500. The pawl 510 is biased by gravity and a spring so that at rest, the lower arm 520 of the pawl 510 is in a lowered position with stop 524 resting against the car face 504. Consequently, the upper arm 512 of the pawl 510 is biased in its upright most position.

The pawl 510 has a vertical drive surface 514 formed on left surface (i.e., output side) of upper arm 512 which is adapted to engage the bottom of the rack 100 at one of its eleven ribs 144. The right surface 516 of upper arm 512 is angled such that when the car 500 is driven to the right (i.e., towards the input section 200), the pawl 510 pivots down out of the way whenever it hits anything (e.g., the bottom of the mixer channel 310 or a rack rib 144). This allows the car 500 to run to the right without engaging a rack 100. Consequently, the car 500 is incapable of driving racks 100 to the right into the input shuttle 250.

The car 500 is driven on a rail assembly 550 by a motor 580 coupled to a drive belt 584. The motor 580 is preferably a stepper motor, such as an Oriental Motors Vexta PK264-01B. The drive belt 584 runs across the entire rail 550, through the mixer/aspirator section 300 and reaches out into the input and output shuttles 250 and 450. The drive belt wraps around a pinion 582 mounted to the motor 580 at one end of the rail 550 and an idler 586 mounted at the other end of the rail 550. The drive ratio is one to one with a positioning resolution of 0.122 mm/step increment. Belt tensioning is accomplished by adjusting the mounting of the motor position using motor mounting slots (not shown).

The car 500 is guided along the rail 550 by tracks 570 formed on either side of the rail 550. Four guide wheels 530, each having a V-shaped periphery 532, are mounted to the bottom 506 of car 500 and engage the tracks 570 to guide the car 500 along the rail 550. Also mounted to the bottom of the car 500 is a block 534 which secures the drive belt 584 to the car 500.

Running along the top surface of the rail 550 is a rib 560 which includes bumps 562, 564, 566 and 568. Attached to the bottom arm 520 of the pawl 510 is a pawl wheel 522 which rides along the rib 560. This pawl wheel 522 rides just above the top of rib 560 without touching it except at bumps 562, 564, 566 and 568. When the pawl wheel 522 encounters one of the bumps 562, 564, 566 and 568, it raises the lower arm 520 of the pawl 510, thereby lowering the top arm 512. This feature prevents the pawl 510 from engaging racks 100 at certain points and also allows the pawl 510 to clear various obstacles (e.g., the mixer channel 310 described below) at various points along the rail 500.

A detailed description of the function of each bump 562, 564, 566 and 568 is given below, however, briefly stated, their functions are as follows:

The first bump 562 allows the car 500 to be parked with the drive pawl 510 depressed at the input end of the rail 550. This car position is used after the tube height sensor 590 has been tripped, to allow a user to retrieve the offending rack.

The second bump 564 is located at the input end of the mixer channel 310 and causes the drive pawl 510 to be depressed in order to avoid the lip of the channel 310.

The third bump 566 allows car 500 to be parked with the drive pawl 510 depressed to the input side of the mixer channel slot 314, at the aspirate position. This allows the mixer channel 310 to pass over the drive pawl 510 without interference between index motions and during mixing. This rail bump 566 is sized and positioned to allow the car 500 to complete its input shuttle motion by driving in the left direction onto the rail bump 566 with the rack 100 engaged.

The fourth bump 568 allows the car 500 to be parked with the drive pawl 510 depressed to the output side of the mixer channel slot 314, at the aspirate position. This position allows the mixer channel 310 to pass over the drive pawl 510 without interference between index motions. This rail bump 568 is sized and positioned to allow the car 500 to complete the output staging motion in a single pass, driving a rack 100 with tube position number 10 at the aspirator location.

The home position of car 500 is located near the right end of the rail 550. This position is in the input shuttle 250, further to the input side of the location where the car pawl 510 engages a rack 100 to drive it from the input shuttle 250 to the mixer/aspirator section 300. A high-precision optical sensor 540 is mounted on the rail 550 at the input end-of-travel. This sensor 540 interacts with a flag 542 mounted to the car 500 to act as a car home sensor.

The flag 542 mounted on the car 500 is sized and mounted so that the flag 542 trips the car home sensor 540 at all times between the car's home position and its physical right most end-of-travel. With the car 500 moving toward the left, the car's home position is defined as the point where the trailing edge 544 of the flag 542 leaves the car home sensor 540. The sensor 540 must remain tripped between the car's home position and its physical end-of-travel in the right direction.

The car home sensor and flag mountings may be fixed, so long as they are manufactured with enough position accuracy to guarantee that the car's home position is detected far enough in advance of reaching the physical end-of-travel that the initialization procedure will never inadvertently crash the car 500 into its stops before it can be halted after seeing the flag 542, and when at the home position, the car pawl 510 is fully raised, and is located between rack rib number 3 and 4 of a rack in the input shuttle. The car home sensor of the preferred embodiment is preferably repeatable to within ±2 motor steps.

Figure 15:
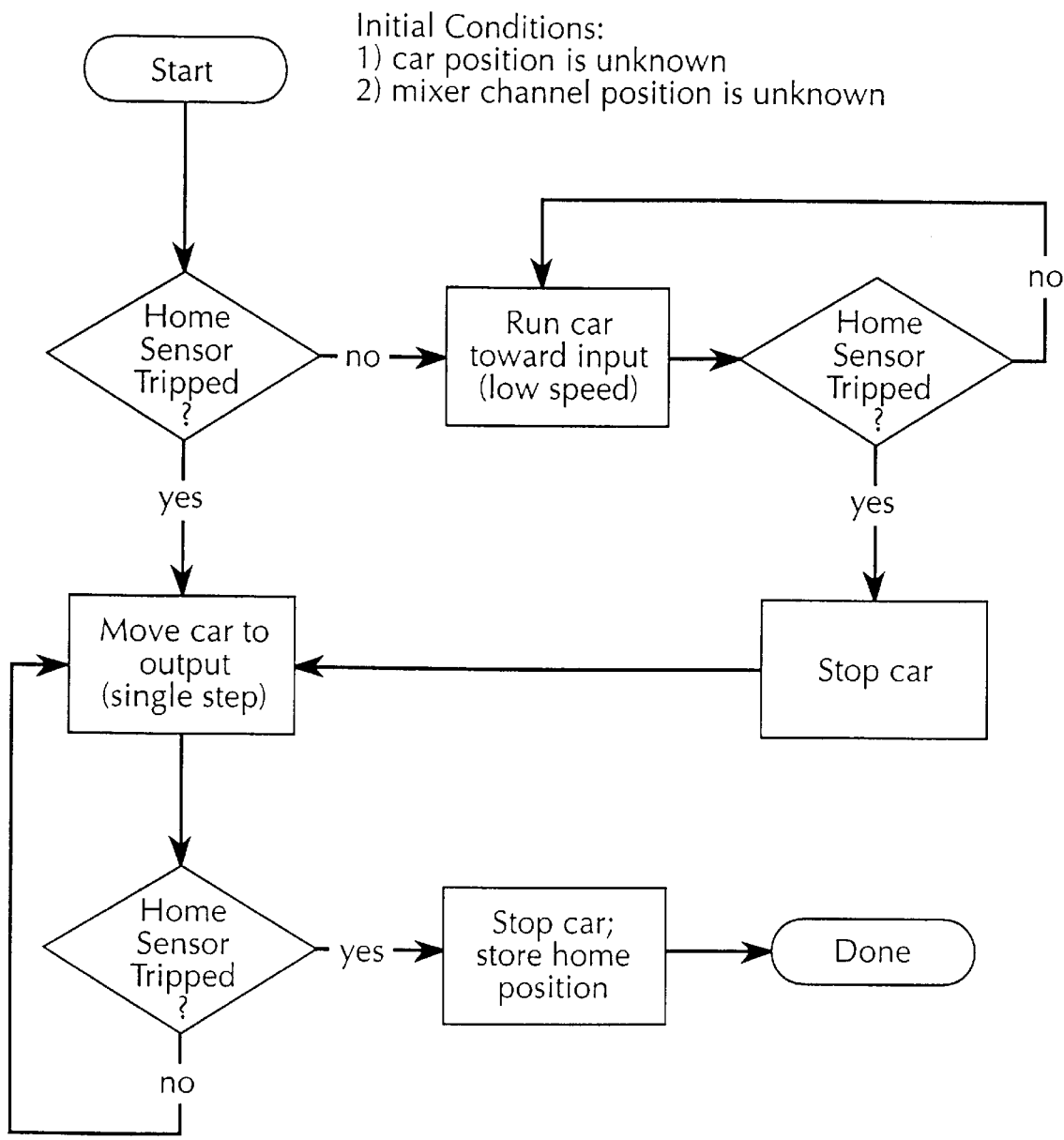
FIG. 15 is a flow diagram of the car mechanism start-up sequence.

The start-up sequence for the car 500 is indicated in FIG. 15. With the car position unknown, the home sensor 540 is first checked to determine if it is tripped. If it is not, the car 500 is run towards the input section 200 at low speed until the home sensor 540 is tripped, at which time the car 500 is stopped. Once the home sensor 540 has been tripped, or if it was tripped initially, the car 500 is then single stepped toward the output section 400 until the home sensor 540 is no longer tripped. The car is then stopped and the home position is stored. The start-up sequence continues by homing the mixer 310 and then clearing any racks 100 present in the mixer 310 to the output shuttle 450.

The car home sensor 540 also enables the system to verify the position of the car 500 during operation and to determine which way to run the car 500 to reach its home position safely at start up. During normal operations, the car 500 is sent to any of its required positions using open-loop relative motion and the car home sensor 540 is monitored for motion verification only. Every time a new rack 100 is to be taken from the input shuttle 250, the car 500 is sent to a position which is a few steps to the input side of the car home position. Then, the car 500 is single-stepped to the left until the home sensor 540 is no longer tripped. If the number of steps moved agrees with the expected number of steps, the car 500 has not lost steps since the last check. If number of steps does not agree with the expected number, the autosampler software may re-home the car 500, and/or the autosampler may declare a system error and shut down.

Located between the input shuttle and the mixer channel 310 is a tube height sensor 590. The tube height sensor 590 is mounted to the input-side side wall 304 of the mixer/aspirator section 300, just above the right side entry port 305 so that tubes too tall to fit in the mixer channel 310 will trip the sensor 590 in time to stop the rack 100 before the offending tube can collide with any part of the autosampler. A sample tube which is not fully inserted into a rack 100 will extend more than the allowable distance above the rack 100 and will also trip the tube height sensor 590.

When a rack 100 with a too-high tube is driven from the input shuttle 250 towards the mixer/aspirator section 300, it trips the tube height sensor 590, which stops the car 500 with minimum deceleration steps to minimize over-travel of the rack 100 and to prevent breaking tubes or damaging the autosampler or rack 100. The car then moves to the first rail bump 562 (i.e., the one at the right most end of the rail, in the input queue) so that the drive pawl 510 will be lowered, thereby allowing the operator to remove or reset the offending rack 100 as appropriate. Tripping of the tube height sensor 590 may also cause notification of the tube height error to an operator workstation, which may be connected to the analyzer and the autosampler.

The Mixer/Aspirator Section

Figure 10:
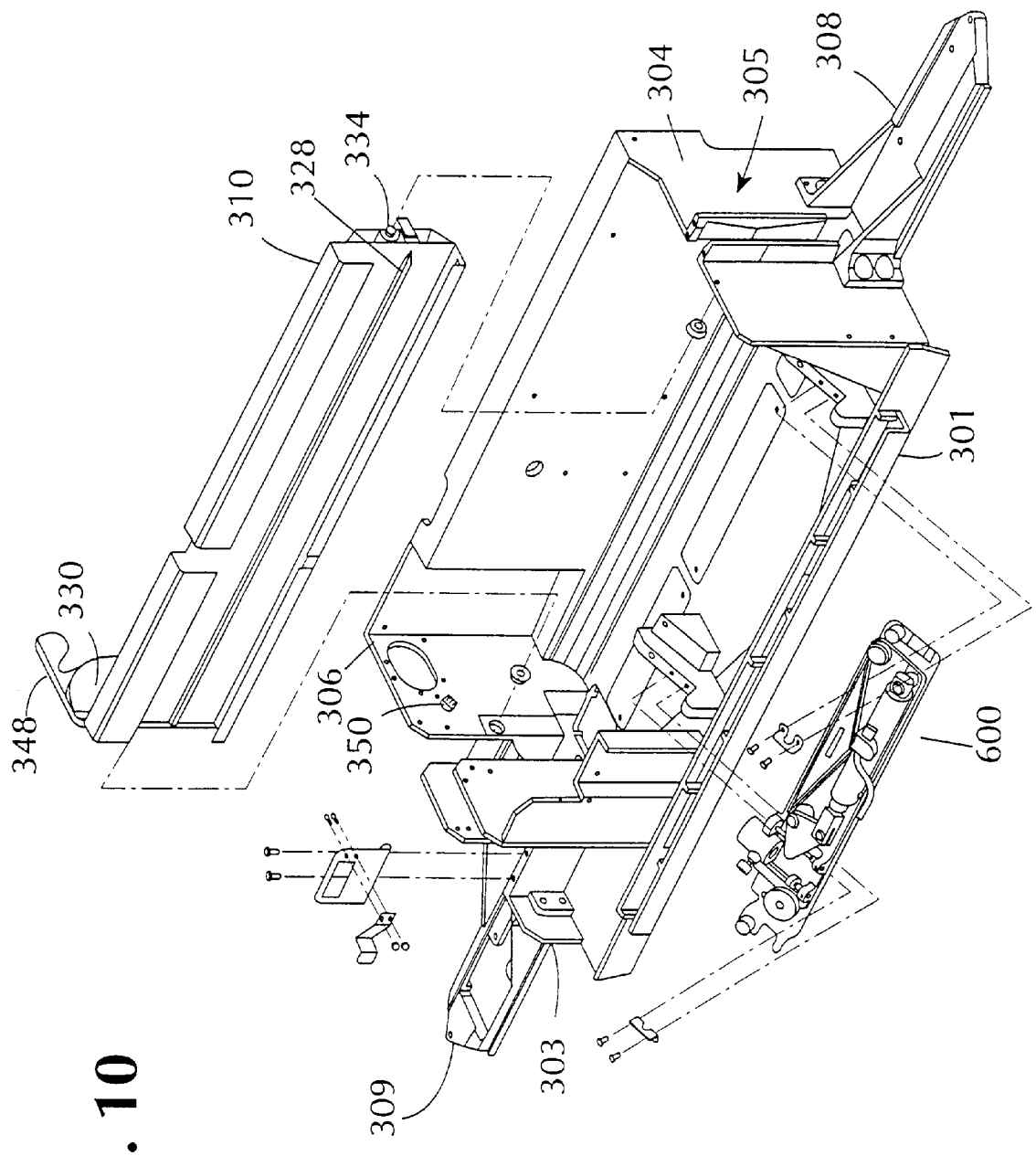
FIG. 10 is a perspective view of the chassis of the mixer/aspirator section of FIG. 9 depicted with the mixer channel and aspirator assembly.
Figure 11:
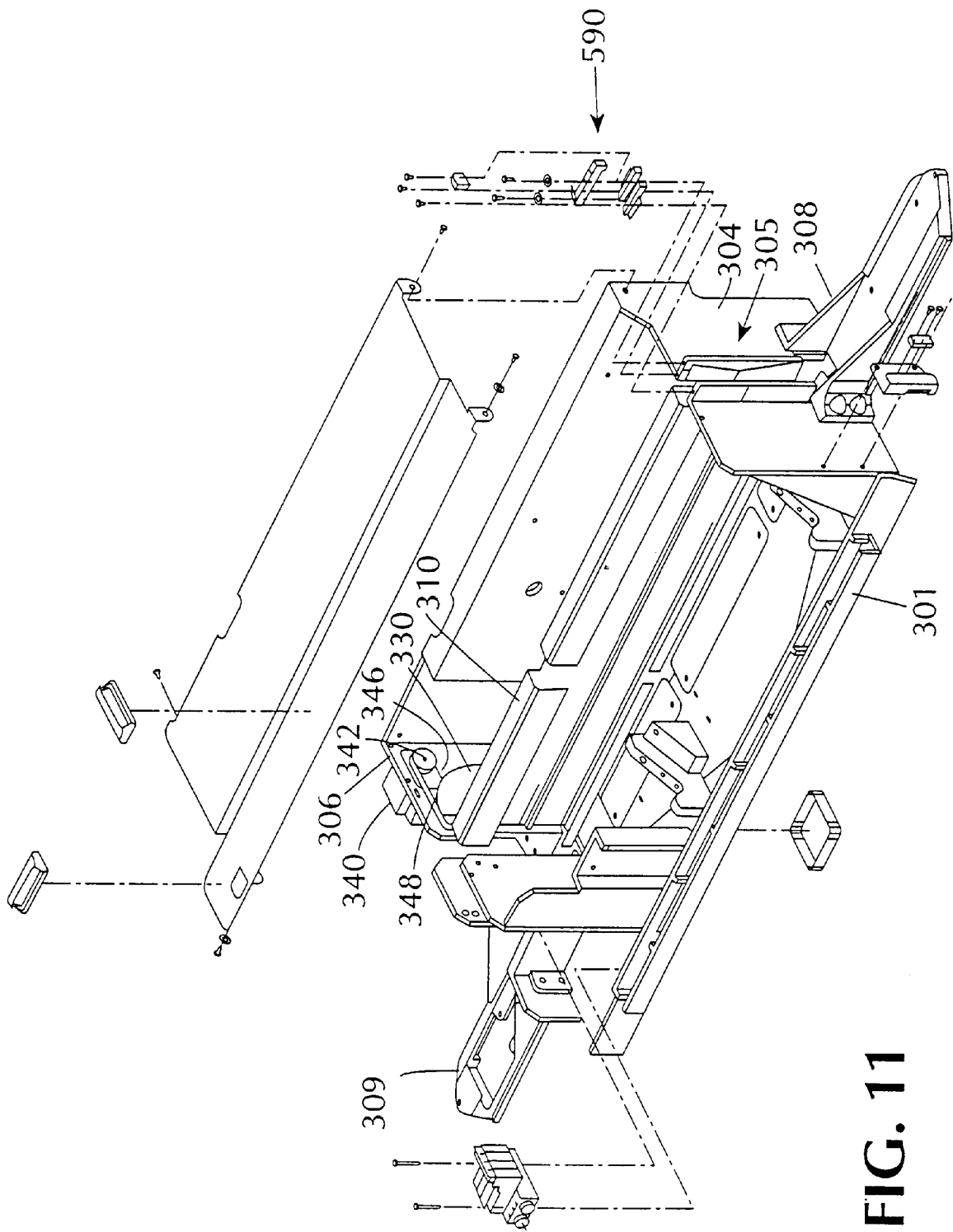
FIG. 11 is a perspective view of the chassis of the mixer/aspirator section of FIG. 9 depicted with the mixer channel and drive assembly in place.

Referring to FIGS. 9–11, the mixer/aspirator section 300 includes a mixer channel 310, an aspirator assembly 600, a push pin assembly 390, an output staging area 364 and a barcode scanner 360. In addition, supports 308 and 309 are mounted to the sides 304 and 303 of the main mixer/aspirator chassis to support the rail assembly 550 as it extends into the input and output sections.

The mixer channel 310 is essentially a pivoted, open-ended channel through which racks 100 pass on the path from input shuttle 250 to output staging area 364. The mixer 310 is capable of mixing the samples contained in the rack 100 by gently rocking them back and forth, positioning the racks 100 so that the barcode labels may be read and positioning the racks 100 so that samples may be aspirated.

The mixer channel 310 has a base 312 which, when the channel 310 is in its shuttle/index position (described below), runs above the rail 550 and is aligned with the bed 252 of the input shuttle 250. Thus racks 100 may be driven laterally from the input shuttle 250 into the mixer channel 310 in the direction of arrow A on FIG. 9. The base 312 of the mixer channel 310 includes a slot 314 everywhere where there is no rail bump on the rail 550. It is through these slots 314 that the car drive pawl 510 engages a rack 100 and drives it from the input shuttle 250, through the mixer channel 310 and towards the output shuttle 450.

Figure 16A:
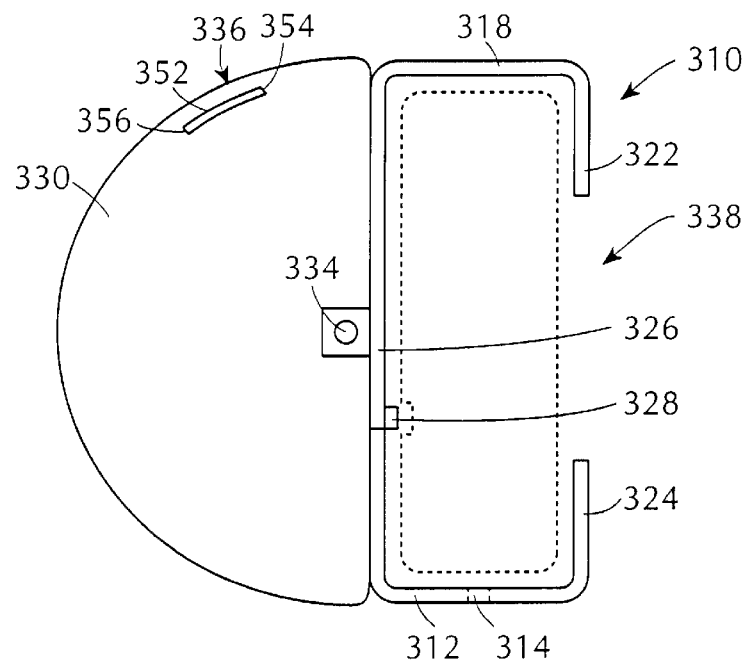
FIG. 16A is side elevational view of the mixer channel of the present invention viewed from the output side.
Figure 16B:
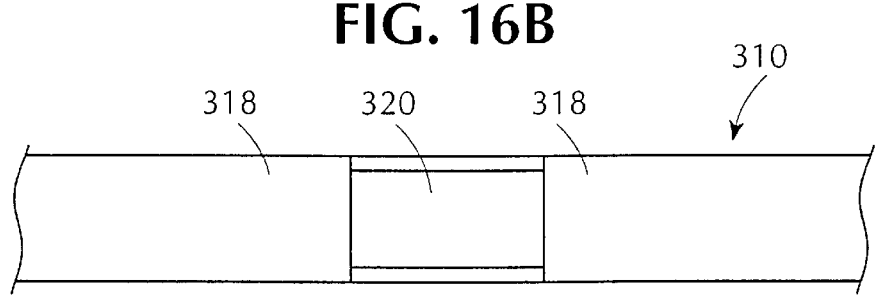
FIG. 16B is a partial top plan view of the mixer channel of the present invention.
Figure 16C:
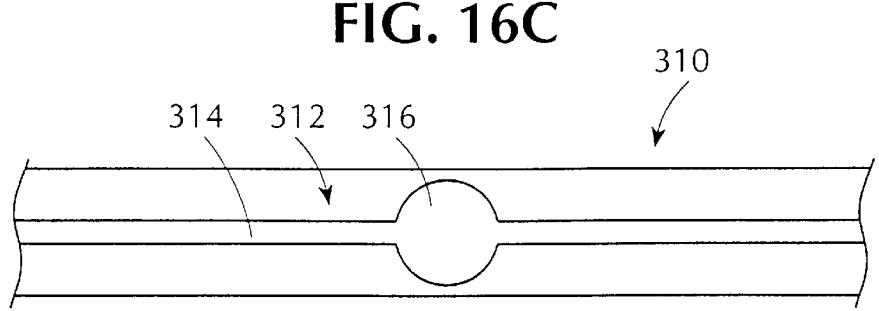
FIG. 16C is a partial bottom view of the mixer channel of the present invention.

As seen in FIGS. 16A–16C, the mixer channel 310 also includes a top wall 318 and a solid back wall 326 connecting the top wall 318 to the base 312. The front of the mixer channel 310 has a top front wall portion 322 and a bottom front wall portion 324 connected to the top wall 318 and the base 312, respectively. The opening 338 thus provided between the top front wall portion 322 and the bottom front wall portion 324 provides access to the rack and sample tube barcode labels so that they may be read by a barcode scanner 360 mounted proximate to the mixer channel 310.

The dimensions of the channel 310, as defined by the base 312 and the top 318, back 326 and front walls 322, 324 are such that the channel 310 can accommodate a rack 100 with tubes of the maximum defined height within the channel 310. In addition, the channel 310 is wide enough so that two racks 100 may be held in it at once.

Springs 328 along the length of the back wall 326 of the channel 310 engage the groove 176 in the back wall 170 of the rack 100 to keep the rack 100 from moving in the vertical direction and to push it against the front walls 322, 324 of the channel 310. The springs 328 also prevent lateral rack 100 movement unless driven by the car drive pawl 510.

The mixer channel 310 is driven to rotate about a shaft 334, which is parallel to the rail 550 and is mounted to the channel 310 proximate to its back wall 326 (FIG. 16A). The motor 340 selected to drive the mixer is the same as the car stepper motor 580 described above and is mounted to the output-side side wall 306. The maximum slew speed required of the mixer is between 2182 and 2600 motor half-steps per second (motor increments/second) from 30 to 100 acceleration steps, respectively. The acceleration rate and speed are selected to minimize resonance effects and audible noise, to meet the throughput requirements, and to avoid damaging blood cells.

Referring to FIGS. 10 and 11, the mixer motor 340 is coupled to the mixer channel 310 using a timing belt 348 driven by a motor pinion gear 342. The timing belt 348 is journaled around a tensioning idler 346 and around the outer perimeter 336 of a sector gear 330. The sector gear 330 is attached to the output side of the mixer channel 310 such that the mixer channel 310 rotates with the sector gear 330 about shaft 334. The total reduction ratio from motor to load is 5.0:1, as set by the ratio of the motor pinion and sector gear diameters.

Table 1 summarizes the mixer channel range of motion and stop positions when viewed from the output section side, with 0° rotation being the rack's upright position and clockwise rotation being positive:

TABLE 1

| Mixer Channel Rotation | |
| --- | --- |
| STOPPED POSITION | ANGLE |
| Shuttle/Index | 0° |
| Top Dwell | +45° |
| Bottom Dwell | +135° |
| Aspirate | +120° |
| Barcode Scan | -20° |

The mixer's shuttle/index position, located at 0° of rotation, is the position in which the mixer channel 310 is aligned with the input shuttle 250. This position allows the car drive pawl 510 to engage a rack 100 in the input shuttle 250 and drive it into the mixer channel 310. This position also allows the car drive pawl 510 to engage a rack 100 already in the mixer channel 310 to index the individual sample tubes into position to have the samples taken by the aspirator assembly 600.

The top and bottom dwell positions (+45° and +135°) are the positions through which the mixer channel 310 rotates back and forth in a periodic rocking motion to mix the samples for processing. The channel 310 can also be oriented for barcode scanning (-20°) and for aspiration (+120°). The barcode scanning position may also be utilized to move the rack 100 clear of the drive pawl 510 if desired. The mixer position requiring the highest precision is aspirate, followed by shuttle/index, barcode scan and the two dwell positions.

The mixer channel's home position is its shuttle/index position (0°). A high-precision sensor 350 mounted to the output-side side wall 306 of the mixer/aspirator section 300 (FIG. 10), proximate to the motor 340, in conjunction with a flag 352 mounted to the sector gear 330 (FIG. 16A), acts as the mixer home sensor. The mixer home flag 352 rotates with the mixer 310 and subtends an arc of just over 20° of mixer rotation. With the mixer channel 310 rotating clockwise as viewed from the output side, the leading edge 354 of the flag 352 trips the home sensor 350 just before the channel 310 reaches the barcode scan position (-20°). Continuing clockwise, the trailing edge 356 of the flag 352 clears the mixer home sensor 350 just after the mixer 310 passes the shuttle/index position (0°). Thus, the mixer home sensor 350 is tripped in both the shuttle/index position and the barcode scan position.

The sensor and flag mountings are fixed, and manufactured with enough position accuracy to guarantee that the sensor 350 is always tripped both when the mixer 310 is in the shuttle/index position and when the mixer is in the barcode scan position, and such that the edge of the flag 352 nearest the home position trips the sensor 350 with a rack 100 hanging out the end of the mixer channel 310 in either direction without damage to the rack 100, sample tubes, or autosampler mechanisms. If the desired position accuracy cannot be reasonably achieved with a fixed mounting, then the mounting of either the sensor or flag must be adjustable. The home sensor is preferably repeatable to within ±2 motor steps (+0.36° of mixer channel rotation).

Figure 17:
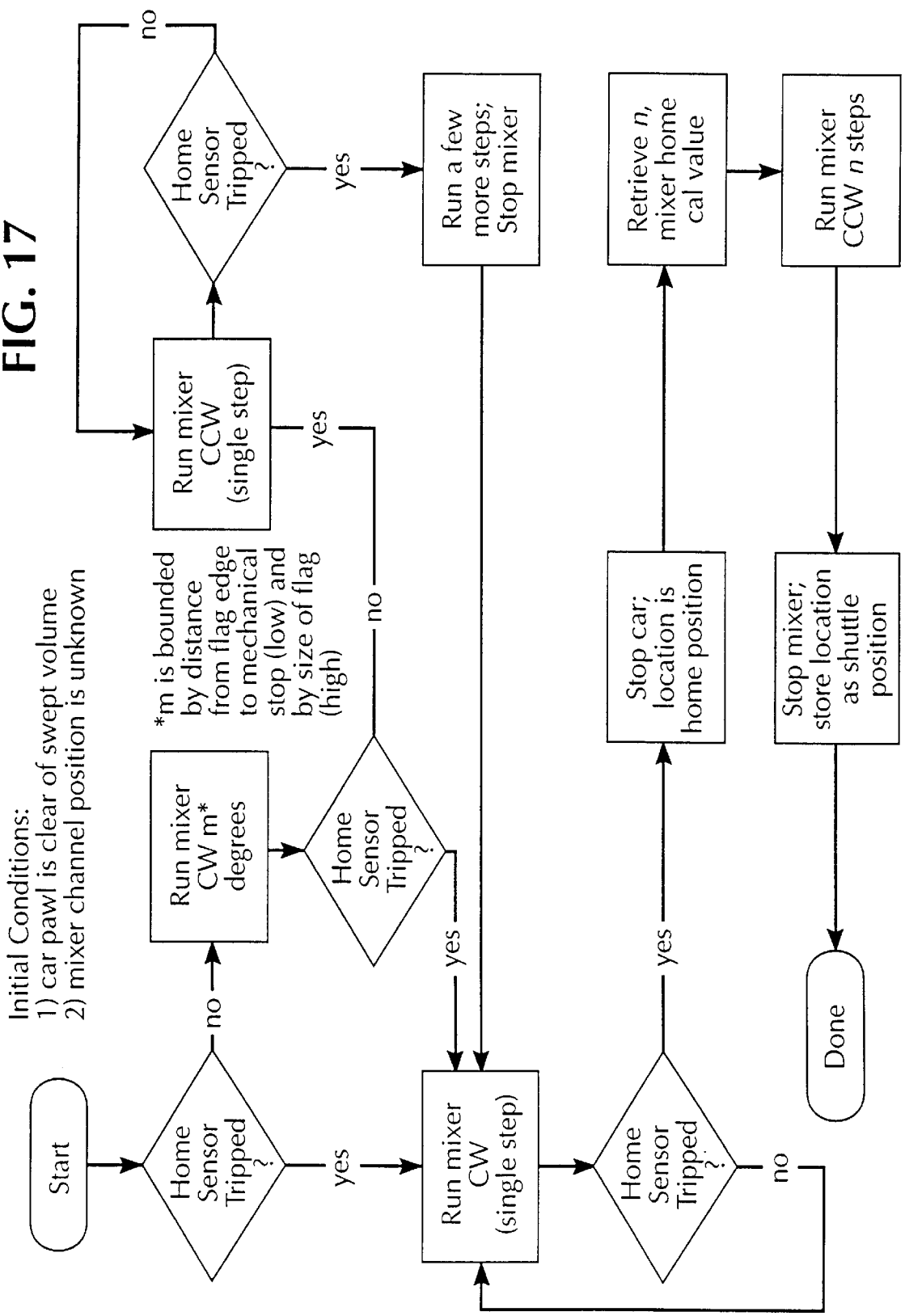
FIG. 17 is a flow diagram of the mixer mechanism start-up sequence.

FIG. 17 illustrates the start-up sequence for the mixer channel 310. It should be noted that the start-up sequence defines the mixer's shuttle position as the orientation of the mixer channel 310 n steps CCW from the position of the mixer 310 when the home sensor 350 detects the trailing edge 356 of the flag 352. This occurs during CW rotation at low speed (also known as the mixer's home position), where n is a calibration constant determined during manufacturing and stored in non-volatile RAM.

It should also be noted that if the sensor 350 is not tripped at start-up, the mixer 310 is moved clockwise a few degrees which is the distance between the mechanical stop and the edge 354 of the flag 352. This accounts for the possibility of starting with the mixer 310 between the −20° and the CCW physical end-of-travel location.

One of the benefits of this scheme is that by reading the mixer home sensor 350 at start-up, it can be determined which way to run the mixer 310 to reach home safely, even with a rack protruding from the end of the mixer channel (i.e., a "jammed" condition). There is inevitably a little "wiggle room" between the rack 100 and channel 310 and between the rack 100 and output staging area 364 or input shuttle 250. The home sensor 350 is read to determine whether to move the mixer 310 CW or CCW to find the home position, which cannot be more than a few steps away with a rack 100 jammed between the mixer 310 and the rest of the system. Finally, the mixer 310 is moved CCW to the shuttle/index position, using the value of n. Once the mixer 310 is stopped at the shuttle/index position, the start-up sequence continues by clearing any racks 100 present in the mixer 310 to the output queue 450. This allows for a safe, simple process to position the mixer 310 at the shuttle/index position during start-up.

As with the car home sensor 540, during normal operations, the mixer home sensor 350 is monitored for motion verification only. Likewise, the mixer 310 is sent to any of its required positions using open-loop relative motion. Every time the mixer 310 stops at the shuttle/index position or the barcode scan position, the home sensor 350 is checked to verify that it is tripped. If it is not tripped, we may conclude that the mixer mechanism has skipped steps and the mixer channel's true position is no longer known. If desired, the autosampler may re-home the mixer 310 and/or declare a system error and shut down.

In operation, after initialization, a rack 100 located in the input shuttle 250 is driven into the mixer channel 310 by the car 500. The car 500 is first positioned at its home position in the input shuttle 250, positioning the drive pawl 510 underneath the third tube receptacle 110 (i.e., between the third and fourth ribs 144) and the mixer 310 rotates to the shuttle/index orientation. The car 500 moves toward the mixer 310 and the drive pawl face 514 engages the rack 100 by the inside face of the third rib 144. The rack 100 is then driven by the car 500 past the tube height sensor 590 and into the mixer channel 310.

Because the slot 314 in the mixer channel 310 ends just short of the input end of the channel 310 for structural reasons, the second rail bump 564 depresses the pawl 510 at this location. The car 500 keeps moving, while the rack 100 stops, and the drive pawl 510 raises up again to engage the first rack rib 144 (i.e., the rib 144 under end wall 120) as the pawl wheel 522 drops off the rail bump 564. The car 500 continues to move to the left, driving the rack 100 by its first rib 144 until the pawl 510 is depressed by the next bump 566, depositing the rack 100 in the mixer channel 310 short of the aspirate position. The car 500 is stopped with the pawl 510 depressed.

As described above, if the tube height sensor 590 trips during this motion the car 500 immediately stops, and then backs up to the first rail bump 562, thereby depressing the drive pawl 510. The operator must then clear the rack 100 containing the offending tube manually because the car 500 is unable to drive the rack 100 to the right.

If the rack 100 does not trip the tube height sensor 590 the rack 100 is driven into the mixer channel 310. As described above, the springs 328 mounted to the back wall 326 of the mixer channel 310 contain and position the rack 100 in the lateral (i.e., left/right) direction and the vertical direction.

Once the rack 100 has been loaded into the mixer channel 310, the samples may then be mixed. To accomplish this, the mixer channel 310 rotates to +45° then to +135°, dwelling in each orientation for an appropriate dwell time and number of mixing cycles. Though the specific dwell times and number of cycles may vary as a matter of design choice, in a preferred embodiment the dwell time at each orientation is a minimum of 0.6 seconds and a maximum of 15 seconds. Further, a total of 45 mix cycles are typically required for each sample before aspiration. Fully mixed samples which experience a dwell of over 15 seconds typically require an additional 20 mix cycles before aspiration. If a dwell exceeds 30 minutes the sample typically must receive a further 45 cycles of mixing before aspiration.

Although the mixer channel 310 may rotate between the barcode scan position (−20°) and the shuttle/index position (0°) when the car 500 is under the mixer channel 310 with the drive pawl 510 raised, the pawl 510 must be depressed for the mixer channel 310 to pass completely over the pawl 510 in the CW direction, i.e., positive rotation past the shuttle/index position. Thus, when the mixer channel 310 is to rotate past 0° rotation (i.e., to mix or aspirate the samples), it is necessary to move the car 500 to the one of the rail bumps 564, 566 or 568 so that the pawl 510 will be depressed, thereby clearing the mixer channel slot 314. Alternatively, the car 500 could be moved left or right beyond the mixer channel 310.

Figure 18:
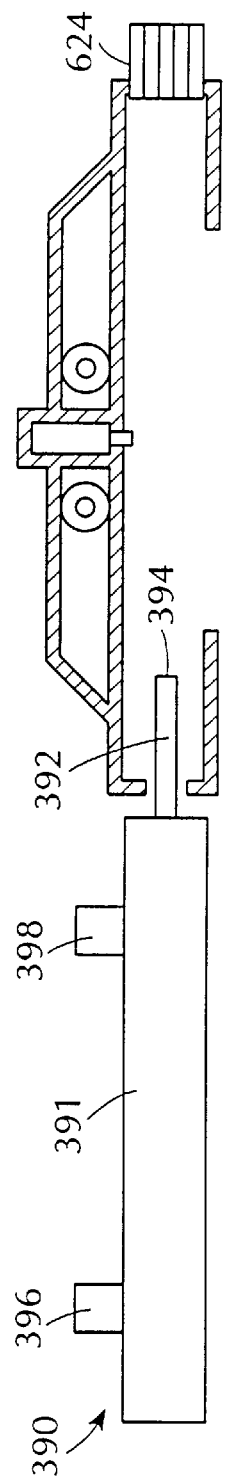
FIG. 18 is a cross sectional view of the mixer channel including a side elevational view of the push pin and aspirator assemblies of the present invention.

After mixing, the mixer channel 310 rotates to place the rack 100, and a sample tube in the rack 100, in the proper orientation for aspiration (i.e., 120°). In this orientation, shown in FIG. 18, the sample tube to be aspirated is positioned in collinear relation with a tube push pin assembly 390 on one side and the aspirator assembly 600 on the other.

The tube push pin assembly 390 is positioned to engage the bottom of the sample tube and to push the sample tube partially out of the rack 100 towards the aspirator assembly 600 until its cap bottoms against the aspirator's centering collar. The drive face 394 of the push pin 392 is designed to accommodate the variety of tube styles, however, it is shaped to avoid penetrating up inside the hollow-bottomed tubes.

As seen in FIG. 16C, the base 312 of the mixer channel 310 at the aspirate position includes an aperture 316 to accept the push pin 392. Likewise, the apertures 142 in the rack's bottom 140 below each tube receptacle 110 are designed to accept the push pin 392. If the push pin 392 jams against the rack 100 or the mixer channel 310, it means either that the rack 100 was not properly positioned laterally within the mixer channel 310, the channel 310 has not been rotated to the proper aspiration orientation or the push pin assembly 390 is not properly aligned.

A pair of Hall Effect sensors 396 and 398 mounted on the tube push pin cylinder 391 are used to determine if a tube is present in the rack 100 at the aspirate location or if a jam condition, described above, exists. The first Hall Effect sensor, the jam sensor 396, is mounted on the tube push pin cylinder 391 in a position to be triggered once the push pin 392 has been extended a minimum distance. This minimum distance is determined to be the distance a successful push pin extension would travel to extend trough the mixer channel 310 and rack 100 to engage a sample tube. If the push pin jam sensor 396 is not triggered or it is triggered and not released after a specified time, it is assumed that the tube push pin 392 has stopped before this minimum distance has been reached, because it has struck either the mixer channel 310 or the rack 100 before reaching a sample tube, and a jam condition exists.

The second Hall Effect sensor 398 is mounted to the tube push pin cylinder 391 in a position to be triggered at the push pin's end-of-travel. If this sensor 398 is triggered, it may be assumed that the push pin 392 has successfully been extended into the mixer channel 310, but no sample tube was encountered.

Figure 19C:
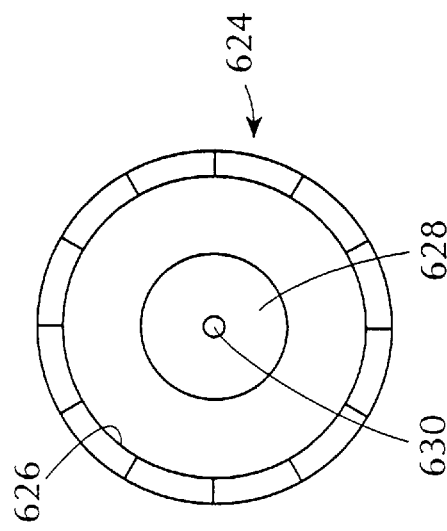
FIG. 19C is an elevational view of the aspirator centering collar of FIG. 19A taken along line C—C.

Mounted on the other side of a sample tube in the aspirate position, is the aspirator assembly 600. The aspirator assembly 600, depicted in FIGS. 19A–19C, contains two mechanisms, a centering collar 624 and an aspirate needle 632.

The centering collar 624, which comprises a cylindrical cavity 626 with a bull-nosed protuberance 628 at the bottom (FIG. 19C), moves out from its home position to provide a reference plane against which the top of the tube cap is pushed by the push pin 392. The aspirate needle 632, which protrudes through a hole 630 in the center of the bull-nosed protuberance 628 when the centering collar 624 is extended, is then extended to pierce the tube cap. The aspiration needle's penetration depth is 17.75 mm beyond the tip of the centering collar's bull nose 628 and, as indicated above, the sample tube is aspirated at a mixer position of 120°.

Figure 19A:
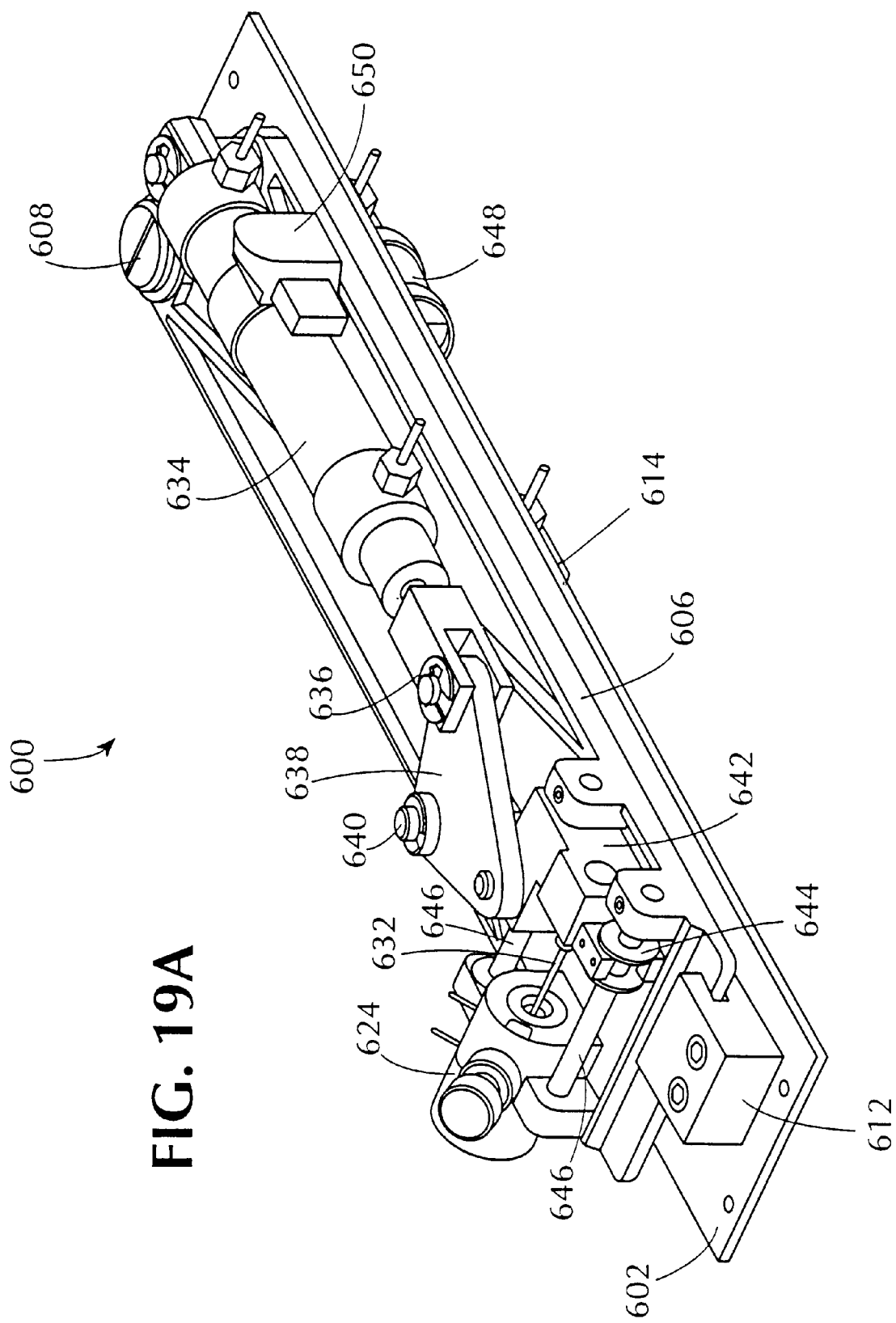
FIG. 19A is a perspective view of the aspirator assembly of the present invention.
Figure 19B:
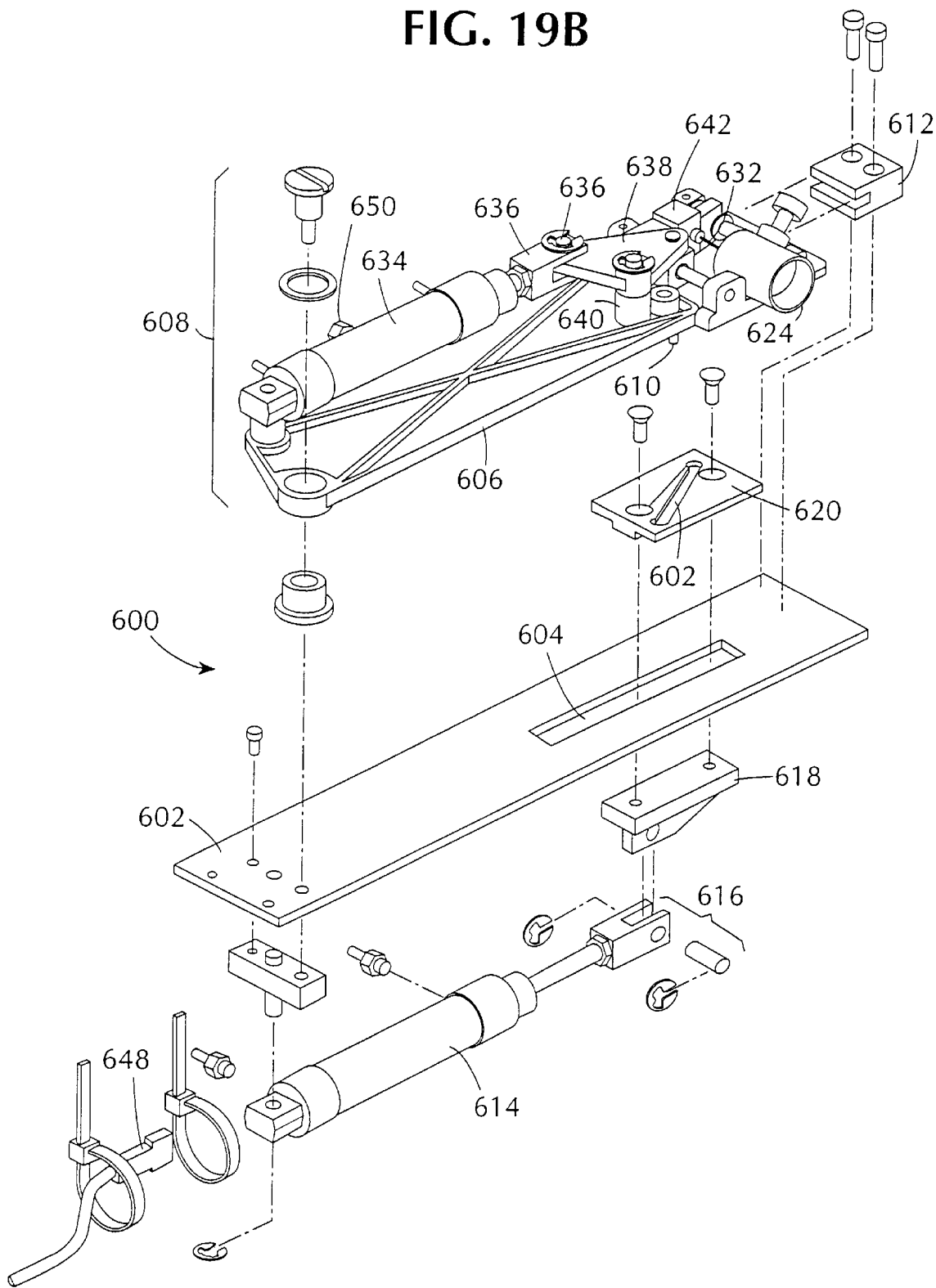
FIG. 19B is an exploded perspective view of the aspirator assembly of FIG. 19A.

Referring to FIGS. 19A and 19B, the illustrated embodiment uses two air cylinders 614 and 634 to extend and retract the centering collar 624 and the aspiration needle 632, respectively. The first air cylinder 614 is mounted to the bottom of a stationary base plate 602 and is connected by a clevis and pin assembly 616 to a cam bracket 618. The cam bracket 618 extends through slot 604 in the base plate 602 and is mounted to the cam 620 on the other side of the base plate 602. Thus, the cam 620 moves back and forth in response to the air cylinder 614 being extended and retracted. A Hall Effect sensor 648 mounted to the air cylinder 614 is used to verify proper operation of the collar mechanism and to verify that the aspirator centering collar 624 is in the extended position.

Mounted to the top of the base plate 602 on top of the cam 620 is the aspirator casting 606, which includes the centering collar 624 at one end. The aspirator casting 606 is mounted to the base plate 602 by a pivot bearing assembly 608 at a point distal from the centering collar 624. A guide member 612 retains the end proximate the centering collar 624 against the base plate 602, while allowing the aspirator casting 606 to pivot about bearing 608. A pin 610 disposed on the bottom of the aspirator casting 606 engages a slot 622 in cam 620, thereby causing the aspirator casting 606 to rotate, and hence the centering collar 624 to be extended and retracted, in response to the air cylinder 614 being extended and retracted.

The second air cylinder 634 is mounted to the aspirator casting 606 and is connected by a clevis and pin assembly 636 to one corner of a triangular needle drive lever 638. A second corner of the needle drive lever 638 is mounted to the aspirator casting 606 by a bearing assembly 640 so as to allow pivotal movement of the lever 638 with respect to the aspirator casting 606. The third corner of the needle drive lever 638 is connected to a needle arm 642 which is mounted behind the centering collar 624 to two rods 646 by bearings 644. The two rods 646 run parallel with each other, as well as with the centering collar 624. The needle 632 is supported on the needle arm 642 and extends into the centering collar 624. It can therefore be observed that by extending and retracting the air cylinder 634, the needle 632 may be controllably extended and retracted. A Hall Effect sensor 650 mounted to the air cylinder 634 is used to detect the aspirator needle 632 retracted position to ensure that the needle 632 is completely retracted.

The aspirator assembly 600 may also contains a wash station for the needle with vacuum and wash lines supplied and controlled by the analyzer. The design of the wash manifold, and the needle fluid pathway is described more fully in U.S. patent application Ser. No. 08/688,314, entitled Sample Input Selector Valve With a Geneva Mechanism, filed Jul. 30, 1996 (attorney docket no. 8698/2012, MST 1954), which is incorporated herein by reference.

In operation, the aspirator 600 first extends its centering collar 624 into a cutout 320 in the top 318 of the mixer channel 310 (see, FIG. 16B) by extending air cylinder 614. The push pin 392 then drives the sample tube cap against the centering collar 624. At the completion of this action, the tube cap is still inside the mixer channel 310 and the top of the cap of the sample tube is resting against the centering collar 624.

Once the centering collar 624 and the push pin 392 have been extended, thereby securing the sample tube, the collar extended sensor 648 is checked to verify that the centering collar 624 has been fully extended. The aspirator needle 632 is then extended by extending air cylinder 634, thereby piercing the sample tube's septum to aspirate a sample. The needle 632 is never extended unless the collar 624 is already extended in order to avoid collisions between the needle 632 and mixer channel 310, and between the needle 632 and tubes incorrectly positioned laterally within the rack 100.

After a sample is aspirated from the tube, the needle 632 is retracted, followed by the push pin 392 and centering collar 624. The needle 632 is never retracted unless the collar 624 is fully extended to eliminate pulling an aspirated tube out of the rack 100. The needle retraction sensor 650 is then checked to verify that the aspirator needle 632 has been completely retracted. This prevents sample carryover by detecting if the needle 632 fails to retract, such that it is not properly washed by the wash cycle. Once retracted, the needle 632 may be washed as described in the aforementioned U.S. Ser. No. 08/688,314.

After a sample has been taken from a sample tube, the rack 100 is then indexed to the next sample tube position by the car 500. The mixer channel 310 is first rotated back to the shuttle/index position. The car 500 is then driven toward the output shuttle 450. In doing so, the drive pawl 510 engages a rack rib 144 and moves the rack 100 one tube position toward the output shuttle 450 so that the next sample tube is centered at the aspirate position. The car 500 is then returned to the third rail bump 566, thereby depressing the pawl 510, and the mixer 310 is rotated to the aspirate position. Optionally, the samples may be mixed between individual aspirations to avoid a maximum dwell time (e.g., 15 seconds) and to prepare the next rack, which may already be in the mixer channel 310, for aspiration.

As discussed above, a barcode scanner 360 may be provided and mounted to scan both the sample tube barcode label and the rack ID label (see FIG. 9). The results of the scan may be used by the analyzer to positively identify samples before aspiration. In addition, the scan results may be used by the autosampler to verify index motion. Two times redundancy is preferably employed to minimize the potential for patient misdiagnosis due to erroneous sample ID.

The barcode scanner 360 may be configured to scan the two labels simultaneously or sequentially. Barcode readers manufactured by Opticon, configured to simultaneously scan both the rack and tube labels, have been found to be suitable. Alternatively, other barcode scanners (such as Microscan readers) or other image capture devices may be used. In addition, separate devices may be used to scan the rack labels and the tube labels.

To scan the rack and sample tube labels, the mixer 310 rotates to position the rack 100 for scanning immediately after indexing the rack 100 and before aspiration of the sample. As discussed above, the opening 338 provided between the top front wall portion 322 and the bottom front wall portion 324 provides access to the rack and sample tube barcode labels so that they may be read by the barcode scanner 360. The mixer angle required to read the labels is barcode reader dependent and affects the control software and the size of the mixer flag. For example, using an Opticon scanner, a −20° mixer angle is required.

When samples from each of the tubes in a rack have been aspirated, the autosampler moves the rack clear of the mixer channel to the output staging area 364 (see FIG. 9). The output staging area 364 is a simple fixed channel, similar to the mixer channel 310, oriented to accept racks from the mixer channel 310 at 0° of mixer rotation. Like the mixer channel 310, the output staging area 364 includes a slot to permit the rack drive pawl 510 to drive a rack from the mixer 310 to the staging area 364, and eventually to the output shuttle 450. A rack in the staging area 364 rests on its base 140 and is prevented from tipping by the walls of the staging area 364. A one-way latch mechanism prevents the car 500 or the operator from pushing a rack 100 from the output shuttle 450 into the output staging area 364.

In operation, a rack 100 located with the right most tube at the aspirate position would be positioned to be advanced to the output staging area 364. With the mixer channel 310 oriented away from the shuttle/index position, the car 500 is moved to the third rail bump 566 at the right side of the aspirator, causing the pawl 510 to be depressed. The mixer 310 is rotated to the shuttle/index orientation to line up with the output staging area 364, and the car 500 is moved toward the output queue 450, driving a rack 100 from the mixer 310 to the output staging area 364.

The Output Section

Referring back to FIG. 1, the output section 400 sits to the left of the mixer/aspirator section 300, outside the autosampler's mixer/aspirator enclosure and is similar in configuration to the input section 200, described above. Like the input section 200, the output section 400 includes an output queue 410 and an output shuttle 450 formed in its cover 404, and in the preferred embodiment holds up to fifteen racks 100 of sample tubes, including a rack in the output shuttle 450, after processing by the autosampler.

Figure 20A:
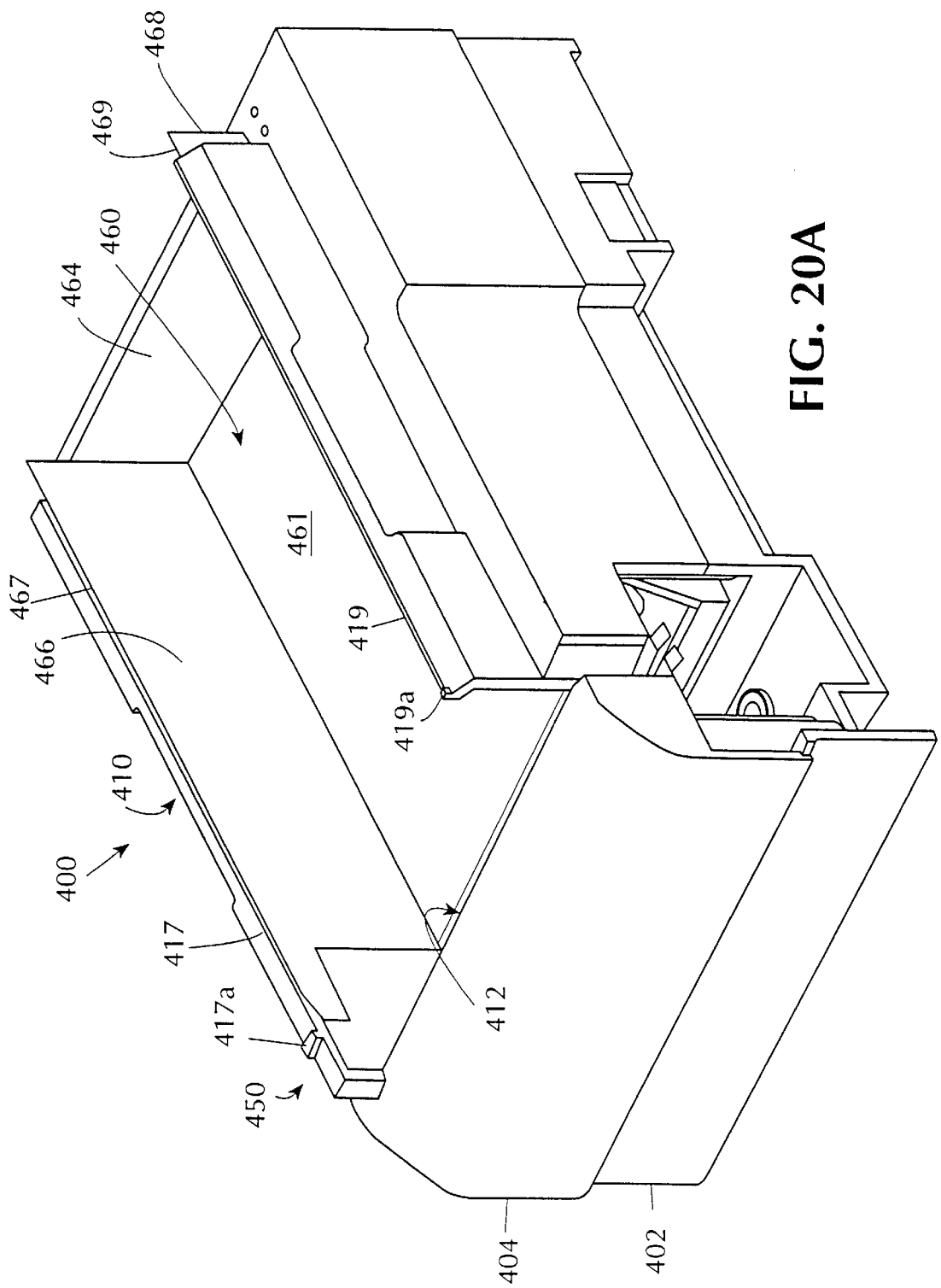
FIG. 20A is a perspective view of the output section of the present invention.
Figure 20B:
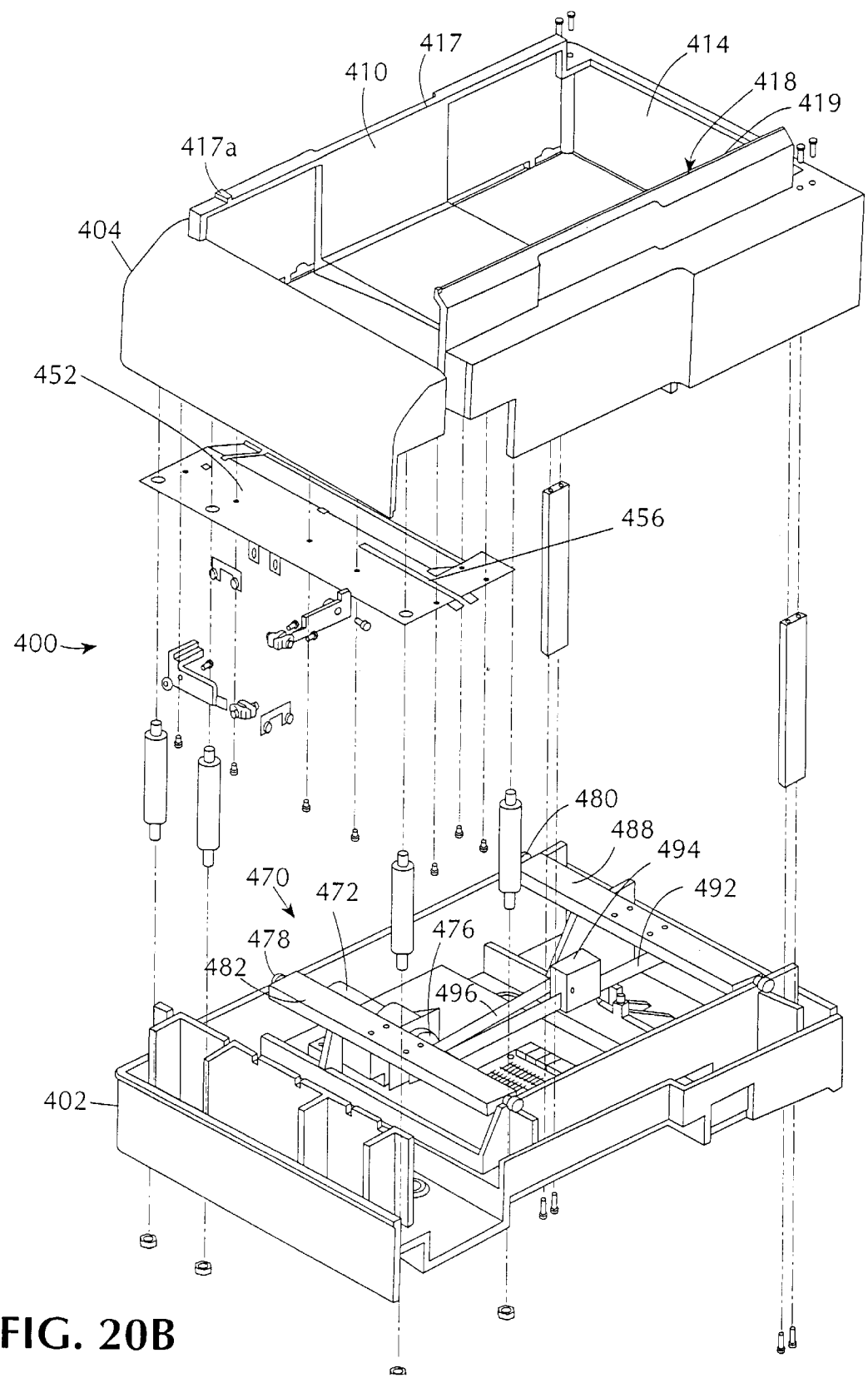
FIG. 20B is a perspective view of the output section of the present invention.

As shown in FIGS. 20A and 20B, the output queue 410 is essentially an open topped box, and like the input queue 210, has a front wall 412, a rear wall 414, two side walls 416 and 418 and a bottom 420. The output queue 410 also includes a pair of stationary guide rails 417 and 419 formed along the top edge of each side 416 and 418, respectively. The racks 100 are supported in the output queue 410 by their ears 124 and 132, in the same manner as described with respect to the input queue 210.

The output shuttle 450 is the front most part of the output queue 410, where racks are driven by the car 500 from the output staging area 364. As in the case of the input shuttle 250, the output shuttle bed 452 is raised slightly with respect to the output queue bottom 420 and a rack 100 in the output shuttle 450 sits on its base and is prevented from tipping in the same manner as a rack in the input shuttle 250. The shuttle bed 452 includes a lateral slot 456 (shown in FIG. 20B) extending into the output shuttle from the side closest to the aspirator/mixer section 300. This slot 456 provides access for the car drive pawl 510 so that a rack 100 may be driven into the output shuttle 450 from the output staging area 364.

The output queue 410 is open at the front and the output shuttle 450 is open at the back, so that racks 100 can pass freely from shuttle 450 to queue 410, similar to the input section 200, except in the reverse direction. A The operator can remove a rack 100 from the output shuttle 450, or from any position within the output queue 410 at any time.

The output queue feed mechanism comprises a pair of walking beams driven by a motor, similar to that described above in connection with the input queue 210. The walking beam drive mechanism 470, however, operates to move racks in the reverse direction from the output shuttle 450 to the output queue 410.

Similar to the input section 200, the illustrated embodiment includes an output queue pan 460 having a bottom 462, a rear wall 464, a front lip 462 and two side walls 466 and 468 disposed within the output queue 410, with the top edges of the queue pan side walls 466 and 468 forming moving rails 467 and 469, respectively. Also as in the case of the input section 200, the output queue pan 460 is supported in the output queue 410 on a pair of lift bars 482 and 488, which are mounted to the base 402 of the output section 400 by respective rods 478 and 480 and connected to each other by a tie rod 492.

The drive motor 472 of the output section 400 is mounted in the same location as in the input section 200, proximate the front lift bar 482, and rotates in the same direction. Likewise, a slider block 494 connected to the cam 476 by a connecting rod 496 engages a feature on the bottom of the queue pan 460 to move the queue pan 460, and hence the moving rails 467 and 469, forward and back. The variable profile cam 476 mounted to the output drive motor 472, however, is configured differently so that the walking beams transport racks in the reverse direction as compared to the input section 200. The connecting rod 496 is connected to the cam 476 at a location such that the slider block 494 is driven rearward, rather than forward, when the lift bars 482 and 488 are raised. Conversely, the slider block 494 is driven forward, rather than rearward, when the lift bars 482 and 488 are lowered.

In operation, the moving rails 467 and 469 of the output queue 410 are driven forward into the output shuttle 450 under the rack's ears 124 and 132, and are raised to lift the rack in the output shuttle 450, as well as any racks already in the output queue 410. The moving rails 467 and 469 are then moved rearward to pull any rack in the shuttle 450 back into the queue 410 and to move the racks already in the output queue 410 further back. Next the moving rails 467 and 469 are lowered and the racks are set down to rest with their ears 124 and 132 supported by the guide rails 417 and 419. Once in the queue 410, protrusions 417a and 419a on the rails 417 and 419 prevent a rack from sliding back into the shuttle 450.

The output shuttle 450 includes an output shuttle full sensor mounted at the left most side of the output shuttle to detect when a rack is in the correct position for feeding into the output queue 410. An additional sensor (the rack clear sensor) mounted just outside the output shuttle 450 at the lateral canter is used to interact with rack rib number six on the bottom of the rack to detect when a rack is not fully clear of the output shuttle 450. Both sensors must be inactive to translate a rack 100 to the left into the output shuttle 450 from the output staging area. If either sensor is active, the rack in the output shuttle 450 must be translated into the output queue using the output queue feed mechanism before a rack in the output staging area may be driven into the output shuttle 450.

In addition, the rack clear sensor also serves the function of detecting when the output queue is no longer able to clear racks from the output shuttle 450 indicating a queue full/jam condition. Normally, a successful queue feed motion takes a rack from the output shuttle 450 and moves it back past the rack clear sensor. If, after a queue feed motion, the sensor is still tripped, the output queue 410 is determined to be full or jammed. In either case, the autosampler may declare a system error and/or shut down.

When the system is first started, or after a reset condition has been detected, the output section 400 must clear racks from the output shuttle 450 to the output queue 410, before racks in the output staging area 364 or mixer/aspirator assembly 300 can be cleared. In normal operation, the output staging area 364 and the output shuttle 450 are aligned to permit a rack to be driven to the left from the output staging area to the output shuttle 450.

The present invention has been described in terms of preferred embodiments thereof, which are provided for purposes of illustration and not of limitation. Other embodiments, features and variations within the scope of the invention will, given the benefit of this disclosure, occur to those having ordinary skill in the art.

What is claimed is:

1. A rack for supporting a plurality of sealed sample tubes, said rack comprising;
   a laterally extending front wall;
   a laterally extending rear wall disposed behind said front wall in a plane substantially parallel to said front wall;
   a plurality of vertical side walls connected to said front wall and said back wall, said side walls being equidistantly spaced apart from each other, thereby defining a plurality of tube receptacles;
   at least one ear mounted to each of an outermost pair of said side walls, wherein said ears are mounted at different vertical heights;
   a horizontal bottom wall connecting said front wall, said back wall and said vertical side walls, said bottom wall including a plurality of equidistantly spaced apertures, each one of said apertures centrally located below one of said tube receptacles;
   a plurality of ribs disposed on said bottom wall, said ribs extending from said front wall to said back wall and being adapted to engage a drive pawl; and
   biasing means disposed within each of said tube receptacles for supporting sample tubes therein.

2. The rack of claim 1 wherein one of said plurality of ribs is disposed between each of said bottom wall apertures.

3. The rack of claim 1 wherein said front wall includes a plurality of windows, each of said windows aligned with one of said tube receptacles such that indicia labels on said sample tubes may be read when said sample tubes are positioned within said rack.

4. The rack of claim 1 further comprising means to center said sample tubes along a plurality of center lines within said tube receptacles.

5. A rack for supporting a plurality of sealed sample tubes having different lengths and different diameters to be mixed and aspirated by an analytical device, said rack comprising;
   a front wall;
   a rear wall disposed behind said front wall;
   a plurality of side walls connected to said front wall and said back wall, said side walls defining a plurality of tube receptacles, each said tube receptacle having a center line;
   at least one ear mounted to each of an outermost pair of said side walls, wherein said ears are mounted at different vertical heights;
   a bottom wall connecting said front wall and said back wall, said bottom wall including a plurality of apertures, each one of said apertures located below one of said tube receptacles;
   a plurality of ribs disposed on said bottom wall; and
   biasing means disposed within each of said tube receptacles for supporting sample tubes therein, wherein said biasing means is adapted to center said sample tubes on said center lines regardless of the length and diameter of the sample tubes within a predetermined range.

6. The rack of claim 5 wherein said biasing means comprises a pair of leaf springs, wherein one of said leaf springs is mounted to each of said vertical side walls defining each of said tube receptacles.

7. The rack of claim 6 wherein each of said leaf springs is generally V-shaped and includes a mounting leg adapted to be secured to one of said side walls and a tube engagement leg adapted to extend into the tube receptacle and engage one of said tubes.

8. The rack of claim 7 wherein the tube engagement leg of each of said leaf springs includes an arcuate shaped tube engagement surface.

9. The rack of claim 5 wherein said ribs are adapted to engage a drive pawl.

10. A rack for supporting a plurality of sealed sample tubes having different lengths and different diameters to be mixed and aspirated by an analytical device, said rack comprising;
   a front wall
   a rear wall disposed behind said front wall;
   a plurality of side walls connected to said front wall and said back wall, said side walls defining a plurality of tube receptacles each, said tube receptacle having a center line;

a bottom wall connecting said front wall and said back wall, said bottom wall including a plurality of apertures, each one of said apertures located below one of said tube receptacles;

a plurality of ribs disposed on said bottom wall; and biasing means disposed within each of said tube receptacles for supporting sample tubes therein, wherein said biasing means is adapted to center said sample tubes on said center lines regardless of the length and diameter of the sample tubes within a predetermined range, said biasing means comprising at least one spring having an arcuate tube engagement surface.

11. A rack for supporting a plurality of sealed sample tubes to be mixed and aspirated by an analytical device, wherein said sample tubes have dimensions within a predetermined range, said rack comprising;

a plurality of walls defining a plurality of tube receptacles, each said tube receptacle having an aperture located below said tube receptacle and a center line within said tube receptacle;

at least one ear mounted to each of an outermost pair of said side walls, wherein said ears are mounted at different vertical heights;

means for engaging a drive pawl mounted to at least one of said walls; and means for suporting said sample tubes within said tube receptacles and centering said sample tubes on said center lines regardless of the dimensions of said sample tubes within said predetermined ranges.

12. The rack of claim 11 wherein said pawl engagement means comprises a plurality of ribs.

13. The rack of claim 11 wherein said sample tube support means comprises at least one leaf spring mounted within each of said tube receptacles.

14. The rack of claim 13 wherein each of said leaf springs is generally V-shaped and includes a mounting leg adapted to be secured to one of said walls and a tube engagement leg adapted to extend into the tube receptacle and engage one of said sample tubes.

15. The rack of claim 14 wherein the tube engagement leg of each of said leaf springs includes an arcuate shaped tube engagement surface.

16. A rack for supporting a plurality of sealed sample tubes to be mixed and aspirated by an analytical device, wherein said sample tubes have dimensions within a predetermined range, said rack comprising:

a plurality of walls defining a plurality of tube receptacles, each said tube receptacle having an aperture located below said tube receptacle and a center line within said tube receptacle;

means for engaging a drive pawl mounted to at least one of said walls; and means for suporting said sample tubes within said tube receptacles and centering said sample tubes on said center lines regardless of the dimensions of said sample tubes within said predetermined ranges, said sample tube support means comprising at least one spring having an arcuate shaped tube engagement surface mounted within each of said tube receptacles.

* * * * *